(12) United States Patent
Chen et al.

(10) Patent No.: US 6,299,877 B1
(45) Date of Patent: Oct. 9, 2001

(54) TYPE I INTERFERONS

(75) Inventors: Jian Chen, Plainsboro, NJ (US); Paul Godowski, Burlingame, CA (US); William I. Wood, Hillsborough, CA (US); Dong-Xiao Zhang, Burlingame, CA (US)

(73) Assignee: Genentech, Inc., So. San Francisco, CA (US)

(*) Notice: Subject to any disclaimer, the term of this patent is extended or adjusted under 35 U.S.C. 154(b) by 0 days.

(21) Appl. No.: 09/206,935

(22) Filed: Dec. 7, 1998

Related U.S. Application Data

(60) Provisional application No. 60/067,897, filed on Dec. 8, 1997, provisional application No. 60/084,045, filed on May 4, 1998, and provisional application No. 60/106,463, filed on Oct. 30, 1998.

(51) Int. Cl.[7] ........................ A61K 39/395; C07K 16/00; C07K 14/00; C12P 21/08

(52) U.S. Cl. ........................ 424/158.1; 424/145.1; 424/139.1; 530/388.23; 530/387.9; 530/388.1; 530/389.1; 530/351

(58) Field of Search ........................ 530/388.1, 389.1, 530/387.9, 351, 388.23; 424/158.1, 145.1, 139.1

(56) References Cited

U.S. PATENT DOCUMENTS 4,423,147  12/1983  Secher et al. .

FOREIGN PATENT DOCUMENTS

| 307247 | 3/1989 | (EP) . |
|---|---|---|
| 032134 B2 | 10/1993 | (EP) . |
| 2079291 | 1/1982 | (GB) . |
| 2123835 | 2/1984 | (GB) . |
| 2161270 | 1/1986 | (GB) . |
| 2161487 | 1/1986 | (GB) . |
| WO 93/04699 | 3/1993 | (WO) . |

OTHER PUBLICATIONS

Adams et al., "Use of a random human BAC end sequence database for sequence–ready map building" (EMBL Database Entry Accession No. AQ111637) (Se. 4, 1998).

Alkan and Braun, "Epitope mapping of human recombinant interferon alpha molecules by monoclonal antibodies" Synthetic peptides as antigens—Ciba Foundation Symposium 119 119:264–278 (1986).

Barasoain et al., "Antibodies against a peptide representative of a conserved region of human IFN–α. Differential effects on the antiviral and antiproliferative effects of IFN" *Journal of Immunology* 143 (2):507–512 (Jul. 15, 1989).

Baron et al., "From cloning to a commercial realization: human alpha interferon" *Crit. Rev. Biotech.* 10 (3):179–190 (1990).

Bolivar et al., "Construction and Characterization of New Cloning Vehicles. II. A Multipurpose Cloning System" *Gene* 2:95–113 (1977).

Capon et al., "Designing CD4 Immunoadhesins for AIDS Therapy" *Nature* 337:525–531 (Feb. 9, 1989).

Capon et al., "Two distinct families of human and bovine interferon–α genes are coordinately expressed and encode functional polypeptides" *Molecular & Cellular Biology* 5:768–779 (1985).

Dafny et al., "Interferon modulates neuronal activity recorded from the hypothalamus, thalamus, hippocampus, amygdala and the somatosensory cortex" *Brain Research* 734 (1–2):269–274 (Sep. 23, 1996).

Darnell et al., "Jak–STAT Pathways and Transcriptional Activation in Response to IFNs and Other Extracellular Signaling Proteins" *Science* 264(5164):1415–1421 (1994).

De Boer et al., "Construction of a tandem trp–lac promoter and a hybrid trp–lac promoter for efficient and controlled expression of the human growth hormone gene in *escherichia coli*" *Promoter Structure and Function*, Rodriguez et al., New York:Praeger Publishers, Chapter 29, pp. 462–481 (1982).

De Maeyer and De Maeyer–Guignard, "Interferons" *The Cytokine Handbook*, 2nd edition, Chapter 15, pp. 265–288 (1994).

De Maeyer, E., "The Presence and Possible Pathogenic Role of Interferons in Disease" *Interferons and other Regulatory Cytokines*, John Wiley and Sons Publishers, Chapter 16, pp. 380–424 (1988).

Duarte et al., "Anticuerpos monoclonales de raton contra el interferon recombinante alfa 2. Su empleo en la purificacion y deteccion del antigeno" *Interferon y Biotechnologia* (An English language summary appears on the front page of the article) 4(3):221–232 (1987).

Evinger and Pestka, "Assay of growth inhibition in lymphoblastoid cell cultures" *Methods in Enzymology* 79 (Pt B):362–368 (1981).

Exley et al., "A comparison of the neutralizing properties of monoclonal and polyclonal antibodies to human interferon alpha" *Journal of General Virology* 65:2277–2280 (1984).

Farkkila et al., "Clinical spectrum of neurological herpes simplex infection" *Acta Neurologica Scandinavica* 87(4):325–328 (1993).

(List continued on next page.)

Primary Examiner—Yvonne Eyler
Assistant Examiner—Janet L. Andres
(74) Attorney, Agent, or Firm—Atulya R. Agarwal

(57) ABSTRACT

The invention concerns a novel human interferon-ε, originally designated PRO655, and its variants and derivatives. The novel interferon is related to but distinct from members of the IFN-α family and from IFNs-β and -γ. Nucleic acid encoding the novel polypeptide, and methods and means for their recombinant production are also included.

13 Claims, 12 Drawing Sheets

(10 of 12 Drawing Sheet(s) Filed in Color)

OTHER PUBLICATIONS

Feng et al., "Progressive Alignment and Phylogenetic Tree Construction of Protein Sequences" *Methods in Enzymology* 183:375–387 (1990).

Gibbs et al., "A negative regulatory region in the intracellular domain of the human interferon–α receptor" *Journal of Biological Chemistry* 271(45):28710–28716 (Nov. 8, 1996).

Goeddel et al., "Human Leukocyte Interferon Produced by *E. coli* Is Biologically Active" *Nature* 287(5781):411–416 (Oct. 2, 1980).

Goeddel et al., "Synthesis of Human Fibroblast Interferon by *E. coli*" *Nucleic Acids Research* 8(18):4057–4074 (1980).

Goeddel et al., "The structure of eight distinct cloned human leukocyte interferon cDNAs" *Nature* 290:20–26 (1981).

Gray et al., "Expression of Human Immune Interferon cDNA in *E. coli* and Monkey Cells" *Nature* 295:503–508 (Feb. 11, 1982).

Heidemann et al., "Gunstigerer verlauf des herpes zoster bei immunsupprimierten patienten unter behandlung mit fibroblasteninterferon" *Onkologie* (An English language summary appears on the front page of the article) 7:210–212 (1984).

Hertzog et al., "Neutralization of interferon α4 by a monoclonal antibody which blocks signal transduction" *Journal of Interferon Research* (abstract #119–15) 10(Suppl. 1):5170 (1990).

Holmes et al., "Structure and Functional Expression of a Human Interleukin–8 Receptor" *Science* 253(5025):1278–1280 (Sep. 13, 1991).

Knobler et al., "Systemic alpha–interferon therapy of multiple sclerosis" *Neurology* 34:1273–1279 (Oct. 1984).

Knoll and Lichter, "In situ hybridization and detection using nonisotopic probes" *Current Protocols in Molecular Biology* (Unit 14.7.1—14.7.14), Ausubel et al., New York:John Wiley & Sons (1995).

Knoll and Lichter, "In situ hybridization to metaphase chromosomes and interphase nuclei" *Current Protocols in Human Genetics* (Unit 4.3.1–4.3.28), Dracopoli et al., New York:John Wiley & Sons vol. 1 (1995).

Kontsek et al., "Distinct effect of pH 2 on a common antigenic structure found in human interferons–$\alpha_1$ and –$\alpha_2$ in the region 30–35" *Journal of Interferon Research* 11:327–332 (1991).

"Labeling and colorimetric detection of nonisotopic probes" *Current Protocols in Molecular Biology* (Unit 3.18), Ausubel et al., New York:John Wiley & Sons pp. 3–42—3–46 (1997).

Lawn et al., "DNA sequence of two closely linked human leukocyte interferon genes" *Science* 212(4499):1159–1162 (Jun. 5, 1981).

Levy et al., "Cytoplasmic Activation of ISGF3, the Positive Regulator of Interferon–α–Stimulated Transcription, Reconstituted In Vitro" *Genes& Development* 3:1362–1371 (1989).

Lu et al., "Structure–function study of the extracellular domain of the human IFN–α receptor (hIFNAR1) using blocking monoclonal antibodies: the role of domains 1 and 2" *Journal of Immunology* 160(4):1782–1788 (Feb. 15, 1998).

Lund et al., "Novel cluster of α–interferon gene sequences in a placental cosmid DNA library" *Proc. Natl. Acad. Sci. USA* 81(8):2435–2439 (Apr. 1984).

Merigan et al., "Human leukocyte interferon for the treatment of herpes zoster in patients with cancer" *N. Engl. J. Med* 298(18):981–987 (May 4, 1978).

Morehead et al., "Roles of the 29–138 disulfide bond of subtype A of human α interferon in its antiviral activity and conformational stability" *Biochemistry* 23(11):2500–2507 (May 22, 1984).

Nagata et al., "Synthesis in *E. coli* of a polypeptide with human leukocyte interferon activity" *Nature* 284(5754):316–320 (1980).

Nagata et al., "The structure of one of the eight or more distinct chromosomal genes for human interferon–α" *Nature* 287(5781):401–408 (Oct. 2, 1980).

Noll et al., "Production and characterization of four monoclonal antibodies specific for human interferon–alpha–1 and –alpha–2" *Biomedica Biochimica Acta* 48(1):165–176 (1989).

Novick et al., "The human interferon α/β receptor: characterization and molecular cloning" *Cell* 77:391–400 (1994).

Pestka, S., "The human interferon–α species and hybrid proteins" *Seminars in Oncology* 24(3 Supp. 9):S9–4—S9–17 (Jun. 1997).

Pestka, S., "The human interferons—from proteins purification and sequence to cloning and expression in bacteria: before, between, and beyond" *Archives of Biochemistry& Biophysics* 221(1):1–37 (Feb. 15, 1983).

Pfeffer, L., "Biologic activities of natural and synthetic type I interferons" *Seminars in Oncology* 24(3 Suppl 9):S9–63 – S9–69 (Jun. 1997).

Picken et al., "Nucleotide sequence of the gene for heat–stable enterotoxin II of *Escherichia coli*" *Infection and Immunity* 42(1):269–275 (1983).

Plioplys and Massimini, "Alpha/beta interferon is a neuronal growth factor" *Neuroimmunomodulation* 2(1):31–35 (Jan.–Feb. 1995).

Reis et al., "Antigenic characterization of human inteferon derived from amniotic membranes induced by virus" *Journal of Interferon Research* 9(5):573–581 (Oct. 1989).

Rubinstein et al., "Convenient assay for inteferons" *Journal of Virology* 37(2):755–758 (Feb. 1981).

Ruppert et al., "Cloning and Expression of Human $TAF_{II}250$: a TBP–associated Factor Implicated in Cell–cycle Regulation" *Nature* 362:175–179 (1993).

Scholtissek et al., "A cloning cartridge of λ $t_o$ terminator" *Nucl. Acids Res.* 15(7):3185 (1987).

Shearer et al., "Monoclonal antibodies that distinguish between subspecies of human interferon–α and that detect inteferon oligomers" *Journal of Immunology* 133(6):3096–3101 (Dec. 1984).

Sompayrac et al., "Efficient infection of monkey cells with DNA of simian virus 40" *Proc. Natl. Acad. Sci. USA* 78(12):7575–7578 (Dec. 1981).

Stancek et al., "Interferon–neutralizing or enhancing activities in hybridoma cells fluids after in vitro immunization" *Acta Virologica* 36(4):376–382 (Aug. 1992).

Streuli et al., "At least three human type α interferons: structure of α2" *Science* 209(4463):1343–1347 (Sep. 19, 1980).

Taniguchi et al., "Human leukocyte and fibroblast interferons are structurally related" *Nature* 285:547–549 (1980).

Thimmappaya et al., "Adenovirus VAI RNA is required for efficient translation of viral mRNAs at late times after infection" *Cell* 31(3 Pt 2):543–551 (Dec. 1982).

Tsukui et al., "A monoclonal antibody with broad reactivity to human interferon–α subtypes useful for purification of leukocyte–derived interferon" *Microbiology & Immunology* 39(11):1129–1139 (1986).

Ullrich et al., "Nucleotide sequence of a portion of human chromsome 9 containing a leukocyte interferon gene cluster" *Journal of Molecular Biology* 156(3):467–486 (Apr. 15, 1982).

Uze et al., "Genetic transfer of a functional human interferon α receptor into mouse cells: cloning and expression of its cDNA" *Cell* 60:225–234 (1990).

Weissmann et al., "Structure and expression of human IFN–α genes" *Philosophical Transactions of the Royal Society of London—Series B: Biological Sciences* 299(1094):7–28 (Sep. 24, 1982).

Wetzel, R., "Assignment of the disulphide bonds of leukocyte interferon" *Nature* 289(5798):606–607 (Feb. 12, 1981).

Whaley et al., "Identification and cellular localization of unique interferon mRNA from human placenta" *Journal of Biological Chemistry* 269(14):10864–10868 (Apr. 8, 1994).

Zhang et al., "Neuregulin–3 (NRG3): A novel neural tissue–enriched protein that binds and activates ErbB4" *Proc. Natl. Acad. Sci. USA* 94:9562–9567 (Sep. 22, 1997).

Zhang et al., "STAT3 participates in transcriptional activation of the C–reactive protein gene by interleukin–6" *Journal of Biological Chemistry* 271(16):9503–9509 (Apr. 19, 1996).

<208 208 residues, 0 stop; molecular weight: 24414.41
1         10        20        30        40        50        60        70
|----------|---------|---------|---------|---------|---------|---------|
MIKHFFGTVLLASTIFSLDLKLIIFQQRQVNQESLKLLNKLQTLSIQQCLPHRKNFLLPQKSLSPQ 71        80        90        100       110       120       130       140
|---------|---------|---------|---------|---------|---------|---------|
QYQKGHTLAILHEMLQQIFSLFRANISLDGWEENHTEKFLIQLHQQLEYLEALMGLEAEKLSGTLGSDNL 141       150       160       170       180       190       200
|---------|---------|---------|---------|---------|---------|---------|
RLQVKMYFRRIHDYLENQDYSTCAWAIVQVEISRCLFFVFSLTEKLSKQGRPLNDMKQELTTEFRSPR v v       v v         v v

FIG. 1

DNA50960

CTTAGATATATTAAACTGATAGATAGGATAAGAGATATAAATAATTTAAGATTGCTGATATATGTTT
TAAAATTAATTATTGCTCAAGCATTGTGACAATTACACAGTTCTTAATTGAGGTTTAAA
TTTAGTAGTTTGTAGTATTTAAGTTTTGCCCCTGAATTCTTTATAGGTGCTGATAAGC
CTTTGGTTAAGTTTTACTCCATGAAAGACTATTACTGAAAAAAATGTAATCTCAATAAAA
GAACTTTAATAAGCTTGACTAAATATTTAGAAAGCACATTGTGTTCAGTGAAACTTGTA
TATAATGAATAGAATAATAAGTTATTTGTTGATGACTAGTCTGTAATGCCTCAAGGA
AAGCATACAATGAATAAGTTATTTTGGTACTCCTCAAAATAGCCAACACAATAGGAAA
TGGAGAAAAATGTACTCTGAACACCATGAAAAAGGAACCTGAAAATCTAATGTAAACTT
GGAGAAATGACATTAGAAAACGAAAGCAACAAAGAGAACACTCTCCAAATAATCTGAG
ATGCATGAAAGGCAAACATTCACTAGAGCTGAATTCCCTAGTCTATGCAGGGATAAG
TAGCATATATTTGACCTTCACC
><Met {trans=1-s, dir=f, res=1}>
ATGATTATCAAGCACTTCTTTGAACTGTGTTGGTGCTGCTGGCCTCTACCACTATCTTC
TCTCTAGATTTGAAACTGATTATCTTCCAGCAAGTGAATCAAGAAAGTTTAAAA
CTCTTGAATAAGTTGCAAACCTGTCAATTCAGCAGTGTCTACCACACAGAGAAAACTTT
CTGCTTCCTCAGAGTCTTTGAGTCCTCAGCAGTACCCAAAAGGACACACTCTGGCCATT
CTCCATGAGATGCTTCAGCAGATCTTCAGCCTCTTCAGGGCAAATATTCTCTGATGGT
TGGGAGGAAACCACACGGAGACTGGAAGCAGAGAAATTCCTCAACTTCATCAACAGCTAGAATACCTA
GAAGCACTCATGGGACTGGAAGCAGAGAAGCTAAGTGGTACTTTGGTAGTGATAACCTT
AGATTACAAGTTAAAATGACTCTCCGAAGGATCCATGATTACCTGGAAAACCAGACTAC
AGCACCTGTGCCTGGCCATTGTCCAAGTAGAAATCAGCCGATGTCTGTTCTTGTGTTC
AGTCTCACAGAAAACTGAGCAAACTGAACAAGGAAGACCCCTTGAACGACATGAAGCAAGAGCTT
ACTACAGAGTTTAGAGCCCGAGTAGGTGGAGGGACTAGGAGGACTTCTCCAGACATGAT
TCTTCATAGAGTGGTAATACAATTATAGTACAATCACATTGCTTTGATTTGTTGTATAT
ATATATTATCTGAGTTTAAGATTGTGCATATTGACCACAATTGTTTTATTTGTAAT
GTGGCTTTATATATTCTATCCATTTAAATTGTTGTATGTCAAATAAATTCATTAATA
TGGTTGATTCTTCAAAAAAAAAAAAAAAAAAAAAAAA

```
1001  AGCAGAGAAG CTAAGTGGTA CTTTGGGTAG TGATAACCTT AGATTACAAG TTAAAATGTA CTTCCGAAGG ATCCATGATT ACCTGGAAAA CCAGGACTAC
      TCGTCTCTTC GATTCACCAT GAAACCCATC ACTATTGGAA TCTAATGTTC AATTTTACAT GAAGGCTTCC TAGGTACTAA TGGACCTTTT GGTCCTGATG
 128    A  E  K    L  S  G  T    L  G  S    D  N  L    R  L  Q  V    K  N  Y    F  R  R    I  H  D  Y    L  E  N    Q  D  Y

1101  AGCACCTGTG CCTGGGCCAT TGTCCAAGTA GAAATCAGCC CTTTGTCTTC AGTCTCACAG AAAAACTGAG CAAACAAGGA AGACCCTTGA
      TCGTGGACAC GGACCCGGTA ACAGGTTCAT CTTTAGTCGG GAAACACAAG TCAGAGTGTC TTTTTGACTC GTTTGTTCCT TCTGGGAACT
 161    S  T  C  A    W  A  I    V  Q  V    E  I  S  R    F  V  F    S  L  T  E    K  L  S    K  Q  G    R  P  L  N

1201  ACGACATGAA GCAAGAGAGCTT ACTACAGAGT TTAGAAGCCC GAGGTAGGTG AGGACTTCTC CAGACATGAT TCTTCATAGA GTGGTAATAC
      TGCTGTACTT CGTTCTCGAA TGATGTCTCA AATCTTCGGG CTCCATCCAC TCCTGAAGAG GTCTGTACTA AGAAGTATCT CACCATTATG
 195    D  N  K    Q  E  L    T  T  E  F    R  S  P    R  Q    G  G  R    R  L  L    R  H  D    L  H  R  I    V  I  T

1301  AATTTATAGT ACAATCACAT TGCTTTGATT TTGTGTATAT CTGAGTTTTA AGATTGTGCA TATTGACCAC AATTGTTTTT ATTTTGTAAT
      TTAAATATCA TGTTAGTGTA ACGAAACTAA AACACATATA GACTCAAAAT TCTAACACGT ATAACTGGTG TTAACAAAAA TAAAACATTA

1401  GTGGCTTTAT ATATTCTATC CATTTTAAAT TGTTTGTATG TTCATTAATA TGGTTGATTC TCAAAAAAAA AAAAAAAAAA
      CACCGAAATA TATAAGATAG GTAAAATTTA ACAAACATAC AAGTAATTAT ACCAACTAAG AGTTTTTTTT TTTTTTTTTT

```
  1  AAACTTTCTG CTTCCTCAGA AGTCTTTGAG TCCTCAGCAG TACCAAAAAG GACACACTCT GGCCATTCTC CATGAGAATGC
     TTTGAAAGAC GAAGGAGTCT TCAGAAACTC AGGAGTCGTC ATGGTTTTTC CTGTGTGAGA CCGGTAAGAG GTACTCTACG
  1   N  F  L   L  P  Q  K   S  L  S    P  Q  Q    Y  Q  K  G   H  T  L    A  I  L   H  E  M  L
                                                                          ^49668.p1

81  TTCAGCAGAT CTTCAGCCTC TTCAGGGCAA ATATTTCTCT GGATGGTTGG GAGGAAAACC ACACGGAGAA ATTCCTCATT
     AAGTCGTCTA GAAGTCGGAG AAGTCCCGTT TATAAAGAGA CCTACCAACC CTCCTTTTGG TGTGCCTCTT TAAGGAGTAA
 28   Q  Q  I   F  S  L    F  R  A  N   I  S  L   D  G  W    E  E  N  H   T  E  K    F  L  I

161  CACTTCATC AACAGCTAGA ATACCAGAA GCACTCATGG AGAGAAGCTA AGTGTACTT TGGGTAGTGA
     GTGAAGTAG TTGTCGATCT TATGGATCTT CGTGAGTACC CTGACCTTCG TCTCTTCGAT TCACCATGAA ACCCATCACT
 54   X  L  H  Q   L  E    Y  L  E   A  L  M  G    L  E  A   E  K  L    S  G  T  L   G  S  D
                                                  ^49668.r2
                                                              ^49668.r1

241  TAACCTTAGA TTACAAGTTA AAATGTACTT CCGAAG
     ATTGGAATCT AATGTTCAAT TTTACATGAA GGCTTC
 81   N  L  R   L  Q  V  K   M  Y  F   R
```

FIG. 6

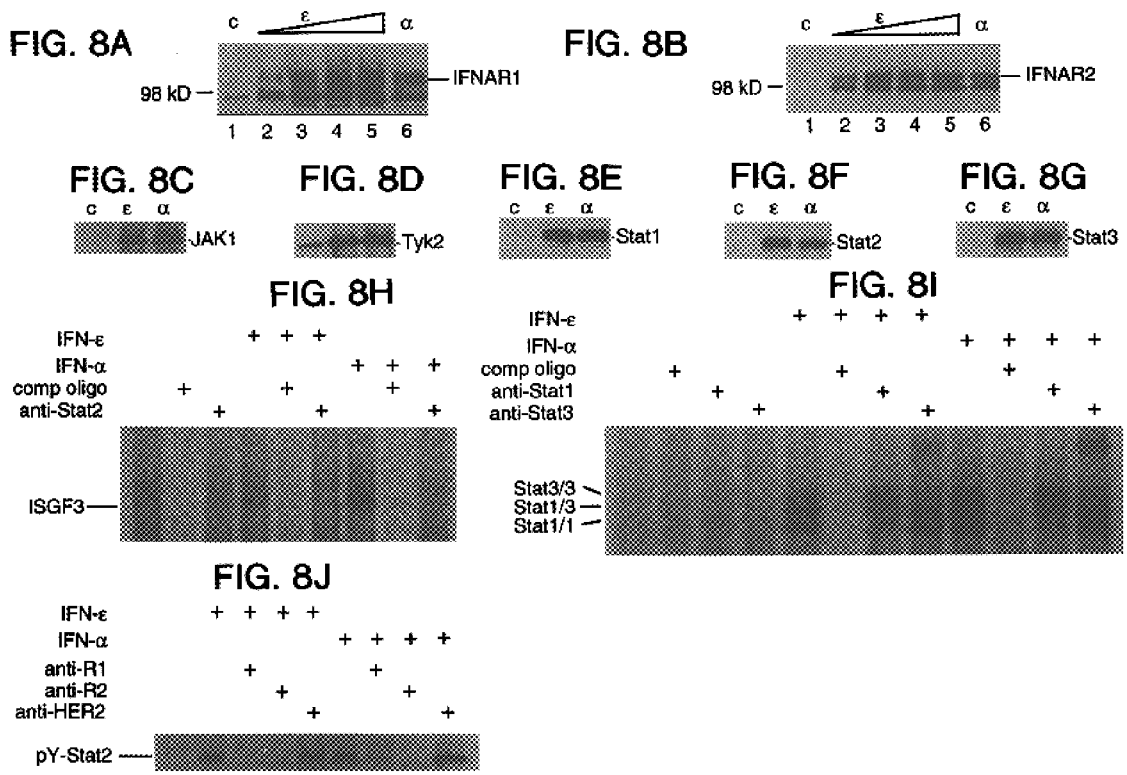

TYPE I INTERFERONS

This is a non-provisional application claiming priority under 35 U.S.C. §119 to provisional application Nos. 60/067,897 filed Dec. 8, 1997; 60/084,045 filed May 4, 1998; and 60/106,463 filed Oct. 30, 1998. The entire disclosure of provisional application No. 60/084,045 is hereby incorporated by reference in its entirety.

FIELD OF THE INVENTION

The present invention relates generally to the identification of a novel member of the type I interferon family. More specifically, the present invention concerns the isolation of a novel nucleic acid encoding a new and distinct type I interferon, termed interferon-epsilon (IFN-ε).

BACKGROUND OF THE INVENTION

Interferons are relatively small, single-chain glycoproteins released by cells invaded by viruses or certain other substances. Interferons are presently grouped into three major classes, designated leukocyte interferon (interferon-alpha, α-interferon, IFN-α), fibroblast interferon (interferon-beta, β-interferon, IFN-β), and immune interferon (interferon-gamma, γ-interferon, IFN-γ). In response to viral infection, lymphocytes synthesize primarily α-interferon (along with a lesser amount of a distinct interferon species, commonly referred to as omega interferon, IFN-ω), while infection of fibroblasts usually induces β-interferon. α- and β-interferons share about 20–30 percent amino acid sequence homology. Thus, the gene for human IFN-β lacks introns, and encodes a protein possessing 29% amino acid sequence identity with human IFN-αI, suggesting that IFN-α and IFN-β genes have evolved from a common ancestor (Taniguchi et al., Nature 285, 547–549 (1980)). By contrast, IFN-γ is not induced by viral infection, rather, is synthesized by lymphocytes in response to mitogens, and is scarcely related to the other two types of interferons in amino acid sequence. Interferons-α, β and ω are known to induce MHC Class I antigens, and are referred to as type I interferons, while IFN-γ induces MHC Class II antigen expression, and is also referred to as type II interferon.

A large number of distinct genes encoding different species of IFNs-α have been identified. Alpha interferon species identified previously fall into two major classes, I and II, each containing a plurality of discrete proteins (Baron et al., Critical Reviews in Biotechnology 10, 179–190 (1990); Nagata et al., Nature 287, 401–408 (1980); Nagata et al., Nature 284, 316–320 (1980); Streuli et al., Science 209, 1343–1347 (1980); Goeddel et al., Nature 290, 20–26 (1981); Lawn et al., Science 212, 1159–1162 (1981); Ullrich et al., J. Mol. Biol. 156, 467–486 (1982); Weissmann et al., Phil. Trans. R. Soc. Lond. B299, 7–28 (1982); Lund et al., Proc. Natl. Acad. Sci. 81, 2435–2439 (1984); Capon et al., Mol. Cell. Biol. 5, 768 (1985)). The various IFN-α species include IFN-αA (IFN-α2), IFN-αB, IFN-αC, IFN-αC1, IFN-αD (IFN-α1), IFN-αE, IFN-αF, IFN-αG, IFN-αH, IFN-αI, IFN-αJ1, IFN-αJ2, IFN-αK, IFN-αL, IFN-α4B, IFN-α5, IFN-α6, IFN-α74, IFN-α76 IFN-α4a), IFN-α88, and alleles of these species. According to our current knowledge, the IFN-α family consists of 13 expressed alleles producing 12 different proteins that exhibit remarkably different biological activity profiles. Pestka, S., Semin. Oncol. 24(suppl. 9), S9-4–S9-17 (1997).

Interestingly, while only a single human IFN-β gene has been unequivocally identified, bovine IFN-β is encoded by a family of five or more homologous, yet distinct genes.

Interferons were originally produced from natural sources, such as buffy coat leukocytes and fibroblast cells, optionally using known inducing agents to increase interferon production. Interferons have also been produced by recombinant DNA technology.

The cloning and expression of recombinant IFN-αA (rIFN-αA, also known as IFN-α2) was described by Goeddel et al., Nature 287, 411 (1980). The amino acid sequences of rIFNs-αA, B, C, D, F, G, H, K and L, along with the encoding nucleotide sequences, are described by Pestka in Archiv. Biochem. Biophys. 221, 1 (1983). The amino acid sequences and the underlying nucleotide sequences of rIFNs-αE, I and J are described in British Patent Specification No. 2,079,291, published Jan. 20, 1982. Hybrids of various IFNs-α are also known, and are disclosed, e.g. by Pestka et al., supra. Nagata et a., Nature 284, 316 (1980), described the expression of an IFN-α gene, which encoded a polypeptide (in non-mature form) that differs from rIFN-αD by a single amino acid at position 114. Similarly, the cloning and expression of an IFN-α gene (designated as rIFN-α2) yielding a polypeptide differing from rIFN-αA by a single amino acid at position 23, was described in European Patent Application No. 32 134, published Jul. 15, 1981.

The cloning and expression of mature rIFN-β is described by Goeddel et al., Nucleic Acids Res. 8, 4057 (1980).

The cloning and expression of mature rIFN-γ are described by Gray et al., Nature 295, 503 (1982).

IFN-ω has been described by Capon et al, Mol. Cell. Biol. 5, 768 (1985).

IFN-τ has been identified and disclosed by Whaley et al., J. Biol. Chem. 269, 10864–8 (1994).

All of the known IFNs-α, -β, and -γ contain multiple cysteine residues. These residues contain sulfhydryl side-chains which are capable of forming intermolecular disulfide bonds. For example, the amino acid sequence of mature recombinant rIFN-αA contains cysteine residues at positions 1, 29, 98 and 138. Wetzel et al., Nature 289, 606 (1981), assigned intramolecular disulfide bonds between the cysteine residues at positions 1 and 98, and between the cysteine residues at positions 29 and 138.

Antibodies specifically binding various interferonsare also well known in the art. For example, anti-α-interferon agonist antibodies have been reported by Tsukui et al., Microbiol. Immunol. 30, 1129–1139 (1986); Duarte et al., Interferon-Biotechnol. 4, 221–232 (1987); Barasoain et al., J. Immunol. 143, 507–512 (1989); Exleyetal., J. Gen. Virol. 65, 2277–2280 (1984); Shearer et al., J. Immunol. 133, 3096–3101 (1984); Alkan et al., Ciba Geigy Foundation Symposium 119, 264–278 (1986); Noll et al., Biomed. Biochim. Acta 48, 165–176 (1989); Hertzog et al., J. Interferon Res. 10(Suppl. 1) 5170 (1990); Kontsek et al., J. Interferon Res. 11 (special issue) 327–332 (1991), and U.S. Pat. No. 4,423,147 issued Dec. 27, 1983.

The actions of type I interferons appear to be mediated by binding to the IFN-α receptor complex on the cell surface. This receptor is composed of at least two distinct proteins identified as IFN-αR1 (Uze et al., Cell 60, 225–234[1990]) and IFN-αR2 (Novick et al., Cell 77, 39–400 [1994]). The engagement of receptors by ligand binding activates Janus family kinases (JAK) and protoplasmic latent signal transducers and activators of transcription (STAT) proteins by tyrosine phosphorylation. Activated STATs translocate to the nucleus in forms of complexes and interact with their cognitive enhancer elements of IFN-stimulated genes (ISGs), leading to a corresponding transcription activation and biological responses. Darnell et al., Science 264, 1415–21 (1994). However, despite similarities in their binding properties, the biological responses stimulated by type I interferons are significantly different.

Interferons have a variety of biological activities, including antiviral, immunoregulatory and antiproliferative properties, and are, therefore, of great interest as therapeutic agents in the control of cancer, and various viral diseases. Interferons have been implicated in the pathogenesis of various autoimmune diseases, such as systemic lupus erythematoses, Behcet's disease, insulin-dependent diabetes mellitus (IDDM, also referred to as type I diabetes). It has been demonstrated in a transgenic mouse model that β cell expression of IFN-α can cause insulitis and IDDM, and IFN-α antagonists (including antibodies) have been proposed for the treatment of IDDM (WO 93/04699, published Mar. 18, 1993). Impaired IFN-γ and IFN-α production has been observed in multiple sclerosis (MP) patients. An acid-labile IFN-α has been detected in the serum of many AIDS patients, and it has been reported that the production of IFN-γ is greatly suppressed in suspensions of mitogen-stimulated mononuclear cells derived from AIDS patients. For a review see, for example, Chapter 16, "The Presence and Possible Pathogenic Role of Interferons in Disease", In: *Interferons and other Regulatory Cytokines,* Edward de pMaeyer (1988, John Wilet and Sons publishers). Alpha and beta interferons have been used in the treatment of the acute viral disease herpes zoster (T. C. Merigan et al., *N. Engl. J. Med.* 298, 981–987 (1978); E. Heidemann et al, *Onkologie* 7, 210–212 (1984)), chronic viral infections, e.g. hepatitis B infections (R. L. Knobler et al., *Neurology* 34, 1273–1279 (1984); M. A. Farkkila et al., *Act. Neurol. Sci.* 87, 325–328 (1993)). rIFN-α-2a (Roferon®, Roche) is an injection formulation indicated in use for the treatment of hairy cell leukemia and AIDS-related Kaposi's sarcoma. Recombinant IFN-α-2b (Intron® A, Schering) has been approved for the treatment of hairy cell leukemia, selected cases of condylomata acuminata, AIDS-related Kaposi's sarcoma, chronic hepatitis Non-A, Non-B/C, and chronic helatitis B infections is certain patients. IFN-γ-1b (Actimmune®, Genentech, Inc.) is commercially available for the treatment of chronic granulomatous disease.

For further information about the biologic activities of type I IFNs see, for example, Pfeffer, *Semin. Oncol.* 24(suppl 9), S9-63–S9-69 (1997).

SUMMARY OF THE INVENTION

Applicants have identified a cDNA clone (designated in the present application as "DNA50960")that encodes a novel human interferon polypeptide, which is now designated as human IFN-ε.

In one embodiment, the invention provides an isolated nucleic acid molecule comprising DNA having at least a 95% sequence identity to (a) a DNA molecule encoding a novel human interferon polypeptide originally designated PRO655, and hereinafter also referred to as IFN-ε, comprising the sequence of amino acids from about 22 to 189 of FIG. 1 (SEQ ID NO: 1), or (b) the complement of the DNA molecule of (a). In one aspect, the isolated nucleic acid comprises DNA encoding a new interferon polypeptide having at least amino acid residues 22 to 189 of FIG. 1 (SEQ ID NO: 1), or is complementary to such encoding nucleic acid sequence, and remains stably bound to it under at least moderate, and optionally, under high stringency conditions. In another embodiment, the isolated nucleic acid molecule encodes the full-length polypeptide represented in FIG. 1 (SEQ. ID. NO: 1), with or without the putative signal peptide at amino acids 1–21, and with or without the initiating methionine, or is the complement of such DNA molecule. In a further embodiment, the isolated nucleic acid molecule comprises DNA having at least a 95% sequence identity to (a) DNA molecule encoding the same mature polypeptide encoded by the human interferon protein cDNA in ATCC Deposit No.209509 (DNA50960-1224), deposited on Dec. 3, 1997.

In another embodiment, the invention provides a vector comprising DNA (as hereinabove defined) encoding a novel interferon-ε polypeptide. A host cell comprising such a vector is also provided. By way of example, the host cells may be CHO cells, *E. coli,* or yeast (including *Saccharomyces cerevisiae* and other yeast strains). A process for producing the new interferon polypeptides of the present invention is further provided and comprises culturing host cells under conditions suitable for expression of the desired interferon polypeptide, and recovering the interferon from the cell culture.

In another embodiment, the invention provides novel, isolated interferon-ε polypeptides. In particular, the invention provides isolated a native interferon-ε polypeptide, which in one embodiment, includes an amino acid sequence comprising residues 22 to 189 of FIG. 1 (SEQ ID NO:1).

In another embodiment, the invention provides chimeric molecules comprising a novel interferon-ε polypeptide herein fused to a heterologous polypeptide or amino acid sequence. An example of such a chimeric molecule comprises an interferon-ε polypeptide fused to an epitope tag sequence or an immunoglobulin heavy or light chain constant region sequence, e.g. the Fc region of an immunoglobulin.

In another embodiment, the invention provides an antibody which specifically binds to a novel interferon-ε polypeptide disclosed herein Optionally, the antibody is a monoclonal antibody.

BRIEF DESCRIPTION OF THE DRAWINGS

The file of this patent contains at least one drawing executed is color. Copies of this patent with color drawings will be provided by the Patent and Trademark Office upon request and payment of the necessary fee.

FIG. 1 shows the derived amino acid sequence of a native sequence human interferon-ε polypeptide, originally designated PRO655. Amino acids 1 to 21 have been identified as a putative signal sequence, using the method of G. von Heijne, *N.A.R.* 14, 4683 (1986).

FIG. 2 shows the nucleotide sequence of a native sequence PRO655 interferon-ε cDNA. The ATG start codon encoding the N-terminal initiating methionine residue is indicated.

FIGS. 3A–B show the nucleotide sequence (SEQ ID NO: 2), complimentary sequence (SEQ ID NO: 3) and the derived amino acid sequence (SEQ ID NO: 1) of the native sequence human interferon-ε polypeptide PRO655.

FIGS. 4A–B are alignments of the amino acid sequence encoded by DNA50960 with known amino acid sequences of human IFNs-β (SEQ ID NO: 7), α1 (SEQ ID NO: 8), α2 (SEQ ID NO: 9, α4 (SEQ ID NO: 10), α5 (SEQ ID NO: 11), α6 (SEQ ID NO: 12), α7 (SEQ ID NO: 13), α8 (SEQ ID NO: 14), αA (SEQ ID NO: 15), αD (SEQ ID NO: 16), αF (SEQ ID NO: 17), αG (SEQ ID NO: 18), and αK (SEQ ID NO: 19). The alignment shows the conservation of the cysteines at positions 53 and 163 in the protein encoded by DNA50960, and indicates a unique cysteine at position 175. There is a potential disulfide bond between positions 53–163 or 53–175.

FIG. 6 shows the nucleotide sequence (SEQ ID NO: 20), complimentary sequence (SEQ ID NO: 21) and the deduced amino acid sequencer (SEQ ID NO: 22) of DNA49668 used in the cloning of DNA50960.

FIG. 8 illustrates that IFN-ε activates tyrosine phosphorylation of IFN-αR1, IFN-αR2 and components in the JAK-STAT pathway. (A) U266 cells were untreated (lane 1) or treated with Histidine (His)-tagged IFN-ε (IFN-ε$^{His}$) of 2 nM, 20 nM, 50 nM and 100 nM (lanes 2, 3, 4, 5, respectively), or with IFN-α$_{2a}$ of $10^3$ U/ml (lanes 6, $10^3$ U/ml ~0.22 nM) for 10 minutes. The cells were lysed and immunoprecipitated by anti-IFN-αR1 antibody (2E1.5.2), probed with peroxidase-conjugated anti-phosphotyrosine antibody 4G10. The molecular weight (MW, in kDa) is indicated at the left. (B) Same treatment as described in (A) except that the cell lysates were immunoprecipitated by anti-IFN-αR2 antibody (3B7.22.7). Equal loading was confirmed by re-probing the blots with corresponding antibodies (data not shown). (C-g) U266 cells were untreated (lane 1), treated with 20 nM of IGN-ε$^{His}$ (lane 2), or with $10^3$ U/ml of IFN-α$_{2a}$ (lane 3) for 15 minutes. The cells were lysed and immunoprecipitated by antibodies against JAK1 (panel C), Tyk2 (panel D), Stat1 (panel E), Stat2 (panel F) and Stat3 (panel G), probed with anti-phosphotyrosine antibody 4G10. Each blot was stripped and probed with antibodies against the corresponding protein and equal loading was confirmed (not shown). (H-I) IFN-ε activates formation of ISGF3 and SIF transcription factor complexes. HeLa cells were either untreated or treated with IFN-ε$^{His}$ (20 nM) or with IFN-α$_{2a}$ (4,000 U/ml) for 45 minutes. Nuclear extract (8 μg of protein) was incubated with about 200 fmol of $^{32}$P-labeled ISRE (panel H) or SIE (panel I) oligonucleotides and analyzed by EMSA. In competition experiments (labeled as "comp oligo"), 50× molar excess of cold oligonucleotides were included in the binding reaction. In supershift experiments (labeled as "anti-State") 1 μg of indicated antibody was employed in the binding reaction (panel J). IFN-αR1 and IFN-αR2 are necessary components for IFN-ε induced signaling. MALT-4 cells ($10^7$ in 1 ml) were pretreated with 10 μg/ml of anti-IFN-αR1 antibody 2E1.5.2 (lanes 3 and 7), or with control anti-HER2 antibody (lanes 5 and 10) for 30 minutes at room temperature and subjected to either no treatment (lane 1) or treatment with IFN-ε$^{His}$ (lanes 2–5) or with IFN-α$_{2a}$ (lanes 6–9). The cells were lysed and immunoprecipitated by anti-State antibody probed with peroxidase-conjugated anti-phosphotyrosine antibody 4G 10.

Figure 5:
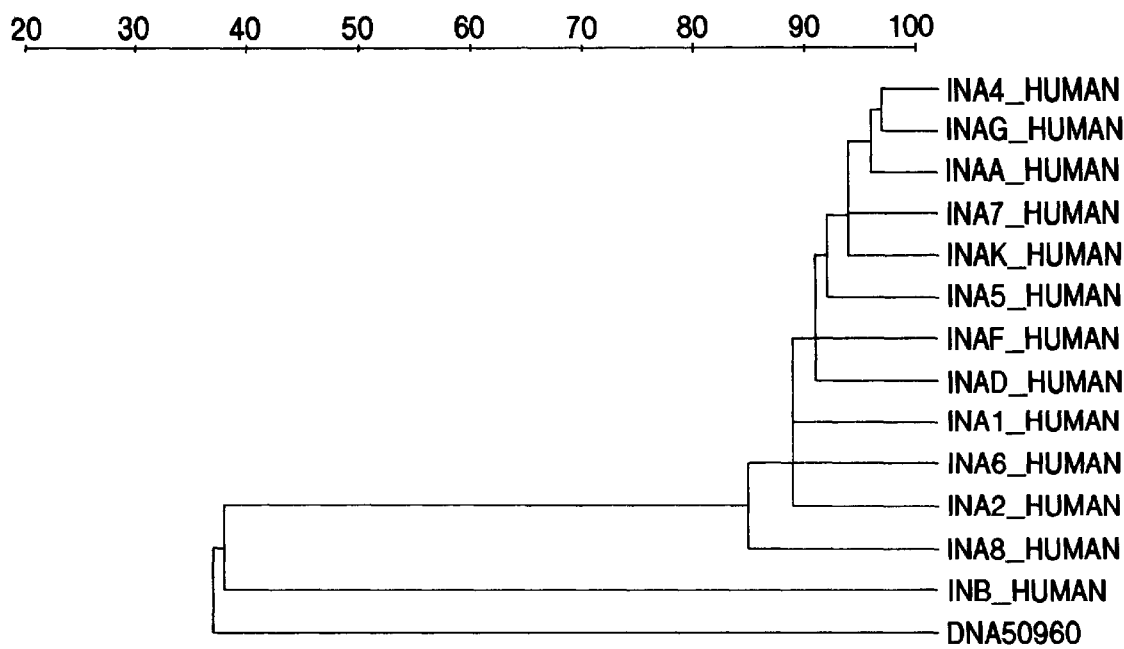
FIG. 5 is a diagram illustrating the relationship of various human a interferons and human interferon with the novel interferon-ε encoded by DNA50960.

DETAILED DESCRIPTION OF THE PREFERRED EMBODIMENTS i. Definitions

The terms "interferon-ε (IFN-ε)", "IFN-ε polypeptide", "PRO655 polypeptide" and "PRO655" when used herein encompass native sequence IFN-ε and IFN-ε variants (which are further defined herein). The novel IFN-ε polypeptide, originally designated PRO655, may be isolated from a variety of sources, such as from human tissue types or from another source, or prepared by recombinant or synthetic methods, or by any combination of these or similar techniques.

A "native sequence interferon-ε (IFN-ε)", or "native sequence IFN-ε polypeptide" or "native sequence PRO655 polypeptide" or "native sequence PRO655", which terms are used interchangeably, comprises a polypeptide having the same amino acid sequence as an IFN-ε polypeptide derived from nature. Such native sequence IFN-ε can be isolated from nature or can be produced by recombinant or synthetic means. The term "native sequence IFN-ε" specifically encompasses naturally-occurring truncated forms of the IFN-ε polypeptide, naturally-occurring variant forms (e.g., alternatively spliced forms) and naturally-occurring allelic variants of the native sequence interferon polypeptide herein. In one embodiment of the invention, the native sequence IFN-ε is a mature or full-length native sequence IFN-ε comprising amino acids 22 to 208 of FIG. 1 (SEQ ID NO:1).

"IFN-ε variant" means an active IFN-ε as defined below encoded by a nucleic acid comprising DNA having at least about 80% nucleic acid sequence identity to (a) a DNA molecule encoding an IFN-ε polypeptide, with or without its signal sequence, or (b) the complement of the DNA molecule of (a). In a particular embodiment, the "IFN-ε variant" has at least about 80% amino acid sequence identity with the IFN-ε having the deduced amino acid sequence shown in FIG. 1 (SEQ ID NO:1) for a full-length native sequence IFN-ε. Such IFN-ε variants include, for instance, IFN-ε polypeptides wherein one or more amino acid residues are added, or deleted at the N- or C-terminus of the sequence of FIG. 1 (SEQ ID NO:1). Preferably, the nucleic acid or amino acid sequence identity is at least about 85%, more preferably at least about 90%, and even more preferably at least about 95%.

"Percent (%) amino acid sequence identity" with respect to the IFN-ε sequences identified herein is defined as the percentage of amino acid residues in a candidate sequence that are identical with the amino acid residues in the IFN-ε sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. In a preferred embodiment, alignment is done using the ALIGN software.

"Percent (%) nucleic acid sequence identity" with respect to the IFN-ε coding sequences identified herein is defined as the percentage of nucleotides in a candidate sequence that are identical with the nucleotides in the IFN-ε coding sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the ALIGN software is used to determine nucleic acid sequence identity.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the IFN-ε natural environment will not be present. Ordinarily, however, isolated polypeptide will be prepared by at least one purification step.

An "isolated" nucleic acid molecule encoding IFN-ε is a nucleic acid molecule that is identified and separated from at least one contaminant nucleic acid molecule with which it is ordinarily associated in the natural source of the IFN-ε-encoding nucleic acid. An isolated nucleic acid molecule is other than in the form or setting in which it is found in nature. Isolated nucleic acid molecules encoding IFN-ε therefore are distinguished from the IFN-ε-encoding nucleic acid molecule as it exists in natural cells. However, an isolated nucleic acid molecule encoding IFN-ε includes nucleic acid molecules contained in cells that ordinarily express IFN-ε where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antbody" is used in the broadest sense and specifically covers single anti-IFN-ε monoclonal antibodies (including agonist, antagonist, and neutralizing antibodies) and anti-IFN-ε antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Active" or "activity" for the purposes herein refers to form(s) of IFN-ε which retain the biologic and/or immunologic activities of native or naturally-occurring IFN-ε. A preferred biological activity is the ability to activate components of the JAC-STAT signaling pathway, and typical specific activities include, but are not limited to, antiviral, immunoregulatory or antiproliferative properties.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and the immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, igG-3, or igG-4 subtypes, IgA (including IgA-1 and IgA-2), IgE, IgD or IgM.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial biological effect for an extended period of time.

"Mammal" for purposes of treatment refers to any animal classified as a mammal, including humans, domestic and farm animals, and zoo, sports, or pet animals, such as dogs, cats, cows, horses, sheep, pigs, etc. Preferably, the mammal is human.

Administration "in combination with" one or more further therapeutic agents includes simultaneous (concurrent) and consecutive administration in any order.

The term "antagonist" is used in the broadest sense, and includes any molecule that blocks, prevents, inhibits, or neutralizes a biological activity of a native IFN-ε polypeptide. In a similar manner, the term "agonist" is used in the broadest sense and includes any molecule that mimics, or enhances a biological activity of a native IFN-ε polypeptide. Suitable agonist or antagonist molecules specifically include agonist or antagonist antibodies or antibody fragments, fragments or amino acid sequence variants of native IFN-ε polypeptides, peptides, small organic molecules, etc.

The term "epitope tagged" when used herein refers to a chimeric polypeptide comprising an IFN-ε polypeptide fused to a "tag polypeptide." The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

II. Compositions and Methods of the Invention

A. Full-Length Human IFN-ε Polypeptide

The present invention provides newly identified and isolated nucleotide sequences encoding novel human interferon polypeptides originally referred to as PRO655, and now renamed as "IFN-ε". In particular, Applicants have identified and isolated cDNA encoding a novel polypeptide, as disclosed in further detail in the Examples below. Using BLAST and FastA sequence alignment computer programs, Applicants found that a full-length native sequence PRO655 polypeptide (shown in FIG. 1 and SEQ ID NO:1) has about 35–40% amino acid sequence identity with the sequence of various human IFN-α species. Specifically, the sequence identity is about 33% and 37% to IFN-α2 and IFN-β, respectively. The sequence identity with IFN-α14 is 38%. The homology is highest within the 22–189 amino acid region of the sequence of FIG. 1 (SEQ ID NO: 1). At the nucleotide level, the sequence identity with the coding sequence of IFN-α is about 60%. Accordingly, we have concluded that PRO655 is a newly identified, novel member of the human interferon family which may possess antiviral, immunoregulatory and/or antiproliferative activities typical of the human interferon family. The relationship of this distinct, novel human interferon to some known IFN-α species and IFN-β is illustrated in FIGS. 5 and 7.

B. IFN-ε Variants

In addition to the full-length native sequence IFN-ε described herein, it is contemplated that IFN-ε variants can be prepared. IFN-ε variants can be prepared by introducing appropriate nucleotide changes into the DNA encoding IFN-ε, or by synthesis of the desired polypeptide. Those skilled in the art will appreciate that amino acid changes may alter post-translational processes of the IFN-ε, such as changing the number or position of glycosylation sites or altering the membrane anchoring characteristics.

It is well known that interferons tend to oligomerize. Although the etiology of these oligomers is not entire understood, it is believed, that certain oligomeric forms result from two or more interferon molecules becoming irreversibly associated with one another through intermolecular covalent bonding, such as by disulfide linkages. This problems has been observed particularly with respect to leukocyte and fibroblast interferons. (See, e.g. U.S. Pat. No. 4,816,566.) Accordingly, it may be desirable to prepare amino acid variants of the native IFN-ε polypeptides of the present invention in which one or more cysteine residues are deleted or substituted by residues of other amino acids which are incapable of disulfide bond formation. Preferred variants substantially retain, mimic or antagonize the biological activity of the IFN-ε from which they are derived. As noted before, the native IFN-ε sequence includes cysteine residues at positions 53, 163 and 175 in the sequence of FIG. 1 (SEQ ID NO:1). In a preferred embodiment, at least one of the cysteine residues at positions 53, 163, and 175 is replaced by amino acid residues that are incapable of forming intermolecular disulfide bonds.

Variations in the native full-length sequence IFN-ε or in various domains of the IFN-ε described herein, can be made, for example, using any of the techniques and guidelines for conservative and go non-conservative mutations set forth, for instance, in U.S. Pat. No. 5,364,934. Variations may be a substitution, deletion or insertion of one or more codons encoding IFN-ε that results in a change in the amino acid sequence of IFN-ε as compared with the native sequence IFN-ε. Optionally the variation is by substitution of at least one amino acid with any other amino acid in one or more of the domains of IFN-ε. Guidance in determining which amino acid residue may be inserted, substituted or deleted without adversely affecting the desired activity may be found by comparing the sequence of IFN-ε with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of 1 to 5 amino acids. The variation allowed may be determined by systematically making insertions, deletions or substitutions of amino acids in the sequence and testing the resulting variants for activity in the in vitro assay described in the Examples below.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene*, 34:315 (1985)], restriction selection mutagenesis [Wells et al., *Philos. Trans. R. Soc. London SerA*, 317:415 (1986)] or other known techniques can be performed on the cloned DNA to produce the IFN-ε variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant. Alanine is also typically preferred because it is the most common amino acid. Further, it is frequently found in both buried and exposed positions [Creighton, *The Proteins*, (W.H. Freeman & Co., N.Y.); Chothia, *J. Mol. Biol.*, 150:1 (1976)]. If alanine substitution does not yield adequate amounts of variant, an isoteric amino acid can be used.

C. Modifications of IFN-ε

Covalent modifications of IFN-ε are included within the scope of this invention. One type of covalent modification includes reacting targeted amino acid residues of the IFN-ε polypeptide with an organic derivatizing agent that is capable of reacting with selected side chains or the N- or C-terminal residues of IFN-ε. Derivatization with bifunctional agents is useful, for instance, for crosslinking IFN-ε to a water-insoluble support matrix or surface for use in the method for purifying anti-IFN-ε antibodies, and vice-versa. Commonly used crosslinking agents include, e.g., 1,1-bis (diazoacetyl)-2-phenylethane, glutaraldehyde, N-hydroxy-succinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate.

Other modifications include deamidation of glutaminyl and asparaginyl residues to the corresponding glutamyl and aspartyl residues, respectively, hydroxylation of proline and lysine, phosphorylationof hydroxyl groups of seryl or threonyl residues, methylation of the α-amino groups of lysine, arginine, and histidine side chains [T. E. Creighton, *Proteins: Structure and Molecular Properties,* W.H. Freeman & Co., San Francisco, pp. 79–86 (1983)], acetylation of the N-terminal amine, and amidation of any C-terminal carboxyl group.

Another type of covalent modification of the IFN-ε polypeptide included within the scope of this invention comprises altering the native glycosylation pattern of the polypeptide. "Altering the native glycosylation pattern" is intended for purposes herein to mean deleting one or more carbohydrate moieties found in native sequence IFN-ε, and/or adding one or more glycosylation sites that are not present in the native sequence IFN-ε, and/or altering the nature (profile) of the sugar moieties attached to the polypeptide at various glycosylation sites.

Addition of glycosylation sites to the IFN-ε polypeptide may be accomplished by altering the amino acid sequence. The alteration may be made, for example, by the addition of, or substitution by, one or more serine or threonine residues to the native sequence IFN-ε (for O-linked glycosylation sites). The IFN-ε amino acid sequence may optionally be altered through changes at the DNA level, particularly by mutating the DNA encoding the IFN-ε polypeptide at preselected bases such that codons are generated that will translate into the desired amino acids.

Another means of increasing the number of carbohydrate moieties on the IFN-ε polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.,* pp. 259–306 (1981).

Removal of carbohydrate moieties present on the IFN-ε polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.,* 259:52 (1987) and by Edge et al., *Anal. Biochem.,* 118:131 (1981). Enzymatic cleavage of carbohydrate moieties on polypeptides can be achieved by the use of a variety of endo- and exo-glycosidases as described by Thotakura et al., *Meth. Enzymol.,* 138:350 (1987).

Another type of covalent modification of IFN-ε comprises linking the IFN-ε polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337. For example, PEGylated variants are expected to have a longer half-life and/or shorter clearance than the corresponding, non-PEGylated IFN-ε polypeptide.

The IFN-ε molecules of the present invention may also be modified in a way to form a chimeric molecule comprising IFN-ε fused to another, heterologous polypeptide or amino acid sequence. In one embodiment, such a chimeric molecule comprises a fusion of the IFN-ε with a tag polypeptide which provides an epitope to which an anti-tag antibody can selectively bind. The epitope tag is generally placed at the amino- or carboxyl-terminus of the IFN-ε. The presence of such epitope-tagged forms of the IFN-ε can be detected using an antibody against the tag polypeptide. Also, provision of the epitope tag enables the IFN-ε to be readily purified by affinity purification using an anti-tag antibody or another type of affinity matrix that binds to the epitope tag.

Various tag polypeptides and their respective antibodies are well known in the art. Examples include poly-histidine (poly-his)or poly-histidine-glycine(poly-his-gly) tags; the flu HA tag polypeptide and its antibody 12CA5 [Field et al., *Mol. Cell. Biol.,* 8:2159–2165 (1988)]; the c-myc tag and the 8F9, 3C7,6E10, G4, B7 and 9E10 antibodies thereto [Evan et al., *Molecular and Cellular Biology,* 5:3610–3616 (1985)]; and the Herpes Simplex virus glycoprotein D (gD) tag and its antibody [Paborsky et al., *Protein Engineering,* 3(6):547–553 (1990)]. Other tag polypeptides include the Flag-peptide [Hopp et al., *BioTechnology,* 6:1204–1210 (1988)]; the KT3 epitope peptide [Martin et al., *Science,* 255:192–194 (1992)]; an α-tubulin epitope peptide [Skinner et al., *J. Biol. Chem.,* 266:15163–15166 (1991)]; and the T7 gene 10 protein peptide tag [Lutz-Freyermuth et al., *Proc. Natl. Acad. Sci. USA,* 87:6393–6397 (1990)].

In another embodiment, the chimeric molecule may comprise a fusion of the IFN-ε with an immunoglobulin or a particular region of an immunoglobulin. For a bivalent form of the chimeric molecule, such a fusion could be to the Fc region of an IgG molecule, to form an "immunoadhesin" as hereinbefore defined. The fusion is preferably to a heavy chain constant region sequence, e.g., a hinge, CH2 and CH3 regions, or the CH1, hinge, CH2 and CH3 regions of an IgG immunoglobulin. Immunoadhesins are expected to have a longer half-life and/or slower clearance than the corresponding IFN-ε polypeptide.

D. Preparation of IFN-ε

The description below relates primarily to production of IFN-ε by culturing cells transformed or transfected with a vector containing nucleic acid encoding IFN-ε. It is, of course, contemplated that alternative methods, which are well known in the art, may be employed to prepare IFN-ε. For instance, the IFN-ε sequence, or portions thereof, may be produced by direct peptide synthesis using solid-phase techniques [see, e.g., Stewart et al., *Solid-Phase Peptide Synthesis,* W.H. Freeman Co., San Francisco, Calif. (1969); Merrifield, *J. Am. Chem. Soc.,* 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of IFN-ε may be chemically synthesized separately and combined using chemical or enzymatic methods to produce the full-length IFN-ε.

1. Isolation of DNA Encoding IFN-ε

DNA encoding IFN-ε may be obtained from a cDNA library prepared from tissue believed to possess the IFN-ε mRNA and to express it at a detectable level. Accordingly, human IFN-ε DNA can be conveniently obtained from a cDNA library prepared from human tissue, such as described in the Examples. The IFN-ε-encoding gene may also be obtained from a genomic library or by oligonucleotide synthesis.

Libraries can be screened with probes (such as antibodies to IFN-ε or oligonucleotides of at least about 20–80 bases)

designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding IFN-ε is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as ALIGN, DNAstar, and INHERIT which employ various algorithms to measure homology.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for IFN-ε production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of transfection are known to the ordinarily skilled artisan, for example, CaPO$_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., *Gene*, 23:315 (1983) and WO 89/05859 published Jun. 29, 1989. For mammalian cells without such cell walls, the calcium phosphate precipitation method of Graham and van der Eb, *Virology*, 52:456–457 (1978) can be employed. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyomithine, may also be used. For various techniques for transforming mammalian cells, see Keown et al., *Methods in Enzymology*, 185:527–537 (1990) and Mansour et al., *Nature*, 336:348–352 (1988).

Suitable host cells for cloning or expressing the DNA in the vectors herein include prokaryote, yeast, or highereukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic microbes such as filamentous fungi or yeast are suitable cloning or expression hosts for IFN-ε-encoding vectors. *Saccharomyces cerevisiae* is a commonly used lower eukaryotic host microorganism.

Suitable host cells for the expression of glycosylated IFN-ε are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Reglicable Vector

The nucleic acid (e.g., cDNA or genomic DNA) encoding IFN-ε may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

IFN-ε may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the IFN-ε-encoding DNA that is inserted into the vector. The signal sequence may be a prokaryotic signal sequence selected, for example, from the group of the alkaline phosphatase, penicillinase, Ipp, or heat-stable enterotoxin 11 leaders. For yeast secretion the signal sequence may be, e.g., the yeast invertase leader, alpha factor leader (including Saccharomyces and Kluyveromyces α-factor leaders, the latter described in U.S. Pat. No. 5,010, 182), or acid phosphatase leader, the *C. albicans* glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the $2\mu$ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the PRO655 nucleic acid, such as DHFR orthymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trpI gene present in the yeast plasmid YRp7 [Stinchcomb et al., *Nature,* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)].

Expression and cloning vectors usually contain a promoteroperably linked to the nucleic acid sequence encoding IFN-ε to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21–25 (1983)]. Promoters for use in bacterial systems also will contain a Shine-Dalgarno (S.D.) sequence operably linked to the DNA encoding IFN-ε.

Examples of suitable promoting sequences for use with yeast hosts include the promoters for 3-phosphoglyceratekinase [Hitzeman et al., *J. Biol. Chem.,* 255:2073 (1980)] or other glycolytic enzymes [Hess et al., *J. Adv. Enzyme Reg.,* 7:149 (1968); Holland, *Biochemistry,* 17:4900 (1978)], such as enolase, glyceraldehyde-3-phosphate dehydrogenase, hexokinase, pyruvate decarboxylase, phosphofructokinase, glucose-6-phosphateisomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, 10 isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

IFN-ε transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the IFN-ε by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the IFN-ε coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding IFN-ε.

Still other methods, vectors, and host cells suitable for adaptation to the synthesis of IFN-ε in recombinant vertebrate cell culture are described in Gething et al., *Nature,* 293:620–625 (1981); Mantei et al., Nature, 281:40–46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA,* 77:5201–5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence IFN-ε polypeptide or against a synthetic peptide based on the DNA sequences provided herein or against exogenous sequence fused to IFN-ε DNA and encoding a specific antibody epitope.

5. Purification of IFN-ε Polypeptide

Forms of IFN-ε may be recovered from culture medium or from host cell lysates. If membrane-bound, it can be released from the membrane using a suitable detergent solution (e.g. Triton-X 100) or by enzymatic cleavage. Cells employed in expression of IFN-ε can be disrupted by various physical or chemical means, such as freeze-thaw cycling, sonication, mechanical disruption, or cell lysing agents.

It may be desired to purify IFN-ε from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the IFN-ε. Various methods of protein purification may be employed and such methods are known in the art and described for example in Deutscher, *Methods in Enzymology*, 182 (1990); Scopes, *Protein Purification: Principles and Practice,* Springer-Verlag, New York (1982). The purification step(s) selected will depend, for example, on the nature of the production process used and the particular IFN-ε produced.

E. Uses for IFN-ε

Nucleotide sequences (or their complement) encoding IFN-ε have various applications in the art of molecular biology, including uses as hybridization probes, in chromosome and gene mapping and in the generation of anti-sense RNA and DNA. IFN-ε encoding nucleic acid will also be useful for the preparation of IFN-ε polypeptides by the recombinant techniques described herein.

The full-length native sequence gene encoding IFN-ε (DNA50960, FIG. 2, SEQ ID NO: 2), or portions thereof, may be used as hybridization probes for a cDNA library to isolate the full-length gene or to o isolate still other genes (for instance, those encoding naturally-occurring variants of IFN-ε or IFN-ε from other species) which have a desired sequence identity to the IFN-ε sequence disclosed in FIG. 2 (SEQ ID NO:2). Optionally, the length of the probes will be about 20 to about 50 bases. The hybridization probes may be derived from the nucleotide sequence of SEQ ID NO: 2 or from genomic sequences including promoters, enhancer elements and introns of native sequence IFN-ε. By way of example, a screening method will comprise isolating the coding region of the IFN-ε gene using the known DNA sequence to synthesize a selected probe of about 40 bases. Hybridization probes may be labeled by a variety of labels, including radionucleotides such as $^{32}$P or 35S, or enzymatic labels such as alkaline phosphatase coupled to the probe via avidin/biotin coupling systems. Labeled probes having a sequence complementary to that of the IFN-ε gene of the present invention can be used to screen libraries of human cDNA, genomic DNA or mRNA to determine which members of such libraries the probe hybridizes to. Hybridization techniques are described in further detail in the Examples below.

The probes may also be employed in PCR techniques to generate a pool of sequences for identification of closely related IFN-ε sequences.

Nucleotide sequences encoding an IFN-ε polypeptide can also be used to construct hybridization probes for mapping the gene which encodes that IFN-ε and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries. Other interferons, e.g. IFNs-α1, α8, α10, α14, α16, α21, β1, and omega1 have been mapped to Chromosome 9.

The novel PRO655 human interferon can also be used in assays to identify and purify its receptor, and to identify other proteins or molecules involved in the ligand/receptor binding interaction. By such methods, inhibitors of the receptor/ligand binding interaction can be identified. Proteins involved in such To binding interactions can also be used to screen for peptide or small molecule inhibitors or agonists of the binding interaction. Screening assays can be designed to find lead compounds that mimic the biological activity of a native PRO655 interferon or a receptor for PRO655. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein—protein binding assays, biochemical screening assays, immunoassays and cell based assays, which are well characterized in the art.

Nucleic acids which encode IFN-ε (PRO655) or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding IFN-ε (PRO655) can be used to clone genomic DNA encoding PRO655 in accordance with established techniques and the genomic sequences used to generate transgenic animals that contain cells which express DNA encoding PRO655. Methods for generating transgenic animals, particularly animals such as mice or rats, have become conventional in the art and are described, for example, in U.S. Pat. Nos. 4,736,866 and 4,870,009. Typically, particular cells would be targeted for PRO655 transgene incorporation with tissue-specific enhancers. Transgenic animals that include a copy of a transgene encoding PRO655 introduced into the germ line of the animal at an embryonic stage can be used to examine the effect of increased expression of DNA encoding PRO655. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of IFN-ε (PRO655) can be used to construct a IFN-ε "knock out"

animal which has a defective or altered gene encoding PRO655 as a result of homologous recombination between the endogenous gene encoding IFN-ε (PRO655) and altered genomic DNA encoding PRO655 introduced into an embryonic cell of the animal. For example, cDNA encoding IFN-ε (PRO655) can be used to clone genomic DNA encoding IFN-ε (PRO655) in accordance with established techniques. A portion of the genomic DNA encoding IFN-ε (PRO655) can be deleted or replaced with another gene, such as a gene encoding a selectable marker which can be used to monitor integration. Typically, several kilobases of unaltered flanking DNA (both at the 5' and 3' ends) are included in the vector [see e.g., Thomas TO and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach,* E. J. 25 Robertson, ed. (IRL, Oxford, 1987), pp. 113–152]. A chimeric embryo can then be implanted into a suitable pseudo pregnant female foster animal and the embryo brought to term to create a "knockout" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions o and for their development of pathological conditions due to absence of the IFN-ε (PRO655) polypeptide.

The novel IFN-ε (PRO655) human interferon polypeptides of the present invention are expected to have antiviral, antiproliferative and/or immunoregulatory activities. Thus, IFN-ε (PRO655), including its variants and derivatives, might be used for the treatment of malignant or non-malignant conditions associated with unwanted cell proliferation, or viral diseases. More particularly, IFN-ε (PRO655) may be useful for the treatment of diseases characterized by tumorigenic or neoplastic cell growth, malignant hematological systemic diseases, viral disease, asthma, carcinomas, sarcomas, myelomas, melanomas, lymphomas, papillomas, degenerative diseases, allergic diseases psoriasis and pain. Dosages can be calculated based upon the specific activity of IFN-ε (PRO655) as compared to the specific activities of other, known interferons, which have been used to treat similar conditions.

F. Anti-IFN-ε Antibodies

The present invention further provides anti-IFN-ε antibodies. Exemplary antibodies include polyclonal, monoclonal, humanized, bispecific, and heteroconjugate antibodies.

1. Polyclonal Antibodies

The anti-IFN-ε antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the IFN-ε polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-IFN-ε antibodies may, alternatively, be monoclonal antibodies. Monoclonal antibodies may be prepared using hybridoma methods, such as those described by Kohler and Milstein, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the anti-IFN-ε polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice,* Academic Press, (1986) pp. 59– 103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyltransferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.,* 133:3001 (1984); Brodeur et al., *Monoclonal Antibody Production Techniques and Applications,* Marcel Dekker, Inc., New York, (1987) pp. 51–63].

The culture medium in which the hybridoma cells are cultured can then be assayed for the presence of monoclonal antibodies directed against anti-IFN-ε. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods [Goding, sugra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Humanized and Human Antibodies

The anti-IFN-ε antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522–525(1986); Riechmann et al., Nature, 332:323–329 (1988); and Presta, Curr. Op. Struct. Biol., 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522–525 (1986); Riechmann et al., Nature, 332:323–327 (1988); Verhoeyen et al., Science, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)). The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86–95 (1991)].

4. Bispecific Antibodies

Bispecific antibodies are monoclonal, preferably human or humanized, antibodies that have binding specificities for at least two different antigens. In the present case, one of the binding specificities is for the IFN-ε, the other one is for any other antigen, and preferably for a cell-surface protein or receptor or receptor subunit. In a further embodiment, one specificity is for IFN-ε, while the other specificity is for type I interferon, preferably IFN-α.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J., 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH 1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioetherbond. Examples of suitable reagents for this purpose include iminothiolate and methyl-4-mercaptobutyrimidate and those disclosed, for example, in U.S. Pat. No. 4,676,980.

G. Uses for anti-IFN-ε Antibodies

The anti-IFN-ε antibodies of the invention have various utilities. For example, anti-IFN-ε antibodies may be used in diagnostic assays for IFN-ε, e.g., detecting its expression in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, *Monoclonal Antibodies: A Manual of Techniques*, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

Anti-IFN-ε antibodies also are useful for the affinity purification of IFN-ε from recombinant cell culture or natural sources. In this process, the antibodies against IFN-ε are immobilized on a suitable support, such a Sephadex resin or filter paper, using methods well known in the art. The immobilized antibody then is contacted with a sample containing the IFN-ε to be purified, and thereafter the support is washed with a suitable solvent that will remove substantially all the material in the sample except the IFN-ε, which is bound to the immobilized antibody. Finally, the support is washed with another suitable solvent that will release the IFN-ε from the antibody.

In the following examples, IFN-ε is shown to be widely expressed in multiple human tissues, and to activate multiple signaling components in the JAK-STAT pathway in a IFNAR-dependent manner. The disclosed results also demonstrate that IFN-ε exhibits anti-growth and immunomodulating effects on cells. In addition, as noted before, interferons have been implicated in the pathogenesis of various autoimmune diseases, such as systemic lupus erythematoses, Behret's disease, insulin-dependent diabetes mellitus (IDDM, also referred to as type I diabetes), and antibodies to various interferons the overexpression of which has been associated with the development and pathogenesis of such diseases have been proposed as potential therapeutics. For example, it has been demonstrated in a transgenic mouse model that β cell expression of IFN-α can cause insulitis and IDDM, and IFN-α antagonists (including antibodies) have been proposed for the treatment of IDDM (WO 93/04699, published Mar. 18, 1993). Accordingly, anti-IFN-ε antibodies might be useful in the treatment of diseases associated with the overexpression of IFN-ε.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Rockville, Md.

Example 1

Isolation of cDNA clones Encoding Human IFN-ε

An expressed sequence tag (EST) DNA database (LIFESEQ™, Incyte Pharmaceuticals, Palo Alto, Calif.) was searched and an EST was identified which showed homology to interferon-α. Possible homology was noted between Incyte EST 3728969 (subsequently renamed as DNA49668) and mammalian alpha interferons, in particular IFN-α14. The homology was confirmed by inspection.

The following PCR primers and oligonucleotide probe were synthesized:
49668.r1:
TCTCTGCTTCCAGTCCCATGAGTGC (SEQ ID NO:4)
49668.r2:
GCTTCCAGTCCCATGAGTGCTTCTAGG (SEQ ID NO:5)
49668.p1:
GGCCATTCTCCATGAGATGCTTCAGCA-GATCTTCAGCCTCTTCAGGGCM (SEQ ID NO:6)

In order to screen several libraries for a source of a full-length clone, DNA from the libraries was screened using the r1 and r2 probes identified above. A positive library was then used to isolate clones encoding the IFN-ε-encoding gene using the probe oligonucleotide.

Three million clones from a size selected (500–4000 bp) oligo dT primed cDNA library from human small intestine (LIB 99) constructed in a pRK5-based vector screened by hybridization. The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the Sf9 site; see, Holmes et al., *Science*, 253:1278–1280 (1991)) in the unique XhoI an d NotI sites. Only one positive clone was found out of 3.6×10$^5$ cfu. The clone was sequenced in both directions and was found to cover the entire reading frame (ORF). A BAC clone (F480) was identified using the sequence of the IFN-ε (Research Genetics). DNA sequencing of the clone isolated as described above gave the full-length DNA sequence for DNA50960 and the derived protein sequence for IFN-ε (PRO655).

The entire nucleotide sequence of DNA50960 is shown in FIG. 2 (SEQ ID NO:2). Clone DNA50960 contains a single open reading frame with an apparent translational initiation site at nucleotide positions 621–623 (FIG. 2). The predicted polypeptide precursor is 208 amino acids long, of which 21 N-terminal amino acid residues represent a putative signal sequence. Clone DNA50960-1224 (clone F480) has been deposited with ATCC and is assigned ATCC deposit no. 209509, deposited on Dec. 3, 1997.

Figure 7A:
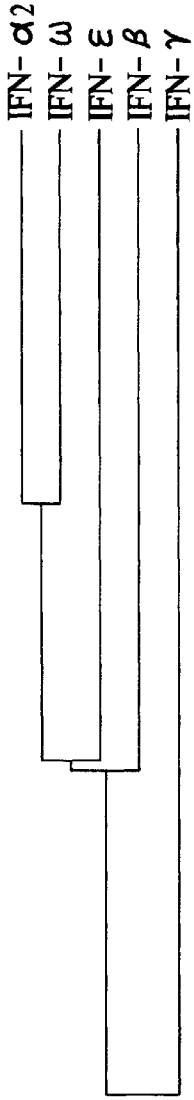
FIG. 7 shows the amino acid sequence analysis, chromosomal localization and mRNA expression of IFN-ε. (A) Protein sequence analysis of IFN-ε. The amino acid sequence alignment analysis for the human type I interferons: IFN-ε (SEQ ID NO: 1), IFN-α2 (SEQ ID NO: 9) (Goeddel et al., Nature 287, 411 (1980)), IFN-β (SEQ ID NO: 7) (Houghton et al., Nucl. Acids Res. 8, 2885–94 (1980)), IFN-ω (SEQ ID NO: 23) (Capon et al., Mol. Cell Biol. 5, 768 (1985)), and IFN-γ (SEQ ID NO: 24) (Whaley et al., J. Biol. Chem. 269, 10864–8 (1994)). Phylogenetic tree of the representative human IFNs is also shown. (B) Chromosomal localization of human IFN-ε. Human metaphase cells were hybridized to a digoxigenin-labeled BAC clone F480 and detected by a fluoresceinated anti-digoxigenin antibody (green) and by a biotin-labeled probe specific for the heterochromatic region of chromosome 9 revealed by Texas-red avidin (red) and counterstained by DAPI. Of a total of 80 metaphase cells analyzed, 72 were specifically labeled.

Using BLAST and FastA sequence alignment computer programs, it was found that PRO655 (shown in FIG. 1 and SEQ ID NO:1) has about 35–40% amino acid sequence identity with the sequence of various human IFN-α species. The homology is highest within the 22–189 amino acid region of the sequence of FIG. 1 (SEQ ID NO: 1). At the nucleotide level, the homology with the coding sequence of IFN-α is about 60%. Based upon these data as well as the presence of a characteristic sequence beginning at amino acid 147 that is typical of type I interferons ([FYH][FY].[GNRC][LIVM].{1}[FY]L.{7}[CY]AW), this molecule was identified as a member of the type I IFN family (FIG. 7). The sequence of IFN-ε is nearly as divergent from IFN-α as it is from IFN-β family members (33% and 37% sequence identity to IFN-α$_{2a}$ and IFN-β, respectively) and thus defines a new branch on the type 1 interferon family tree. Molecular modeling suggests that IFN-ε displays similar tertiary structure compared to IFN-α (L. Presta, data not shown). A diagrammatic comparison of IFN-ε with other IFNs is shown in FIG. 7(A).

Example 2

Use of the Novel Human Interferon Encoding DNA as a Hybridization Probe

The following method describes use of a nucleotide sequence encoding IFN-ε as a hybridization probe.

DNA comprising the coding sequence of IFN-ε (as shown in FIG. 2, SEQ ID NO:2) is employed as a probe to screen for homologous DNAs (such as those encoding naturally-occurring variants of IFN-ε) in human tissue cDNA libraries or human tissue genomic libraries.

Hybridization and washing of filters containing either library DNAs is performed under the following high stringency conditions. Hybridization of radiolabeled probe derived from the PRO655-encoding DNA, to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0. 1% SDS at 42° C.

DNAs having a desired sequence identity with the DNA encoding full-length native sequence IFN-ε can then be identified using standard techniques known in the art.

Example 3

Expression of IFN-ε in *E. coli*

This example illustrates preparation of an unglycosylated form of IFN-ε by recombinant expression in *E. coli*.

The DNA sequence encoding IFN-ε (SEQ ID NO:2) is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli;* see Bolivar et al., *Gene,* 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the IFN-ε coding region, lambda transcriptional terminator, and an argu gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized IFN-ε protein can then be purified using a metal chelating column under conditions that allow tight binding of the protein.

A specific example of the expression and purification of recombinant IFN-ε in *E. coli* is provided in Example 10 below.

Example 4

Expression of IFN-ε in Mammalian Cells

This example illustrates preparation of a glycosylated form of IFN-6 (PRO655) by recombinant expression in mammalian cells.

The vector, pRK5 (see EP 307,247, published Mar. 15, 1989), is employed as the expression vector. Optionally, the IFN-ε-encoding DNA is ligated into pRK5 with selected restriction enzymes to allow insertion of the IFN-ε-encoding DNA using ligation methods such as described in Sambrook et al., supra. The resulting vector is called pRK5-IFN-ε (PRO655).

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-IFN-ε (PRO655) DNA is mixed with about 1 μg DNA encoding the VA RNA gene [Thimmappaya et al., *Cell,* 31:543 (1982)] and dissolved in 500 μl of 1 mM Tris-HCl, 0.1 mM EDTA, 0.227 M CaCl$_2$. To this mixture is added, dropwise, 500 μl of 50 mM HEPES (pH 7.35), 280 mM NaCl, 1.5 mM NaPO$_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}$S-cysteine and 200 µCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of IFN-ε polypeptide. The cultures containing transfected cells may undergo further incubation (in serum free medium) and the medium is tested in selected bioassays.

In an alternative technique, DNA encoding IFN-ε may be introduced into 293 cells transiently using the dextran sulfate method described by Sompayrarac et al., *Proc. Natl. Acad. Sci.*, 78:7575 (1981). 293 cells are grown to maximal density in a spinner flask and 700 µg pRK5-IFN-ε DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed IFN-ε can then be concentrated and purified by any selected method, such as dialysis and/or column chromatography.

In another embodiment, the novel interferon polypeptide (IFN-ε, PRO655) was transiently transfected into COS7 cells. 20 µg of a plasmid encoding IFN-ε under control of the CMV IE promoter, was mixed with 2 µg of a Green Fluorescent Protein (GFP) expressing plasmid. The DNA was introduced into the cells with a commercially available transfection reagent, following manufacturer's instructions. One day post-transfection, the cells were visualized at 425nM, using a fluorescent microscope to ensure a transfection efficiency >25% (25% GFP positive). The medium was then removed and the plates were fed 25 ml of collection media and incubated at 32° C. for 5 days. Collection media: enriched serum-free medium containing 10 ng/ml insulin. Media: high-glucose DMEM (Gibco-BRL) with 0.5% fetal bovine serum. Media were collected, cells and debris removed by centrifugation and filtration through a 0.2 µM sterile filter.

Epitope-tagged IFN-ε DNA may also be expressed in host CHO cells. The IFN-ε DNA may be subcloned out of the pRK5 vector. The subclone insert can undergo PCR to fuse in frame with a selected epitope tag such as a poly-his tag. The poly-his tagged insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged IFN-ε can then be concentrated and purified by any selected method, such as by $Ni^{2+}$-chelate affinity chromatography.

Following essentially the protocol described, a poly-his tagged human IFN-ε polypeptide (PRO713) was prepared and purified. The different PRO number merely indicates that the protein was obtained in a different expression experiment. PRO713 has the same amino acid sequence as PRO655, i.e. is encoded by DNA50960.

Example 5

Expression of IFN-ε in Yeast

The following method describes recombinant expression of IFN-ε in yeast.

First, yeast expression vectors are constructed for intracellular production or secretion of IFN-ε from the ADH2/ GAPDH promoter. DNA encoding IFN-ε, a selected signal peptide and the promoter is inserted into suitable restriction enzyme sites in the selected plasmid to direct intracellular expression of IFN-ε. For secretion, DNA encoding IFN-ε can be cloned into the selected plasmid, together with DNA encoding the ADH2/GAPDH promoter, the yeast alpha-factor secretory signal/leader sequence, and linker sequences (if needed) for expression of IFN-ε.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant IFN-ε can subsequently be isolated and purified by removing the yeast cells from the fermentation medium by centrifugation and then concentrating the medium using selected cartridge filters. The concentrate containing IFN-ε may further be purified using selected column chromatography resins.

Example 6

Expression of IFN-ε in Baculovirus-Infected Insect Cells

The following method describes recombinant expression of IFN-ε in Baculovirus expression system.

The IFN-ε-encoding DNA is fused upstream of an epitope tag contained with a baculovirus expression vector. Such epitope tags include poly-his tags and immunoglobulintags (like Fc regions of IgG). A variety of plasmids may be employed, including plasmids derived from commercially available plasmids such as pVL1393 (Novagen). Briefly, the coding sequence of IFN-ε or the desired portion of the coding sequence is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4–5 days of incubation at 28° C., the released viruses are harvested and used for further amplifications. Viral infection and protein expression is performed as described by O'Reilley et al., Baculovirus expression vectors: A laboratory Manual, Oxford: Oxford University Press (1994).

Expressed poly-his tagged IFN-ε can then be purified, for example, by $Ni^{2+}$-chelate affinity chromatography as follows. Extracts are prepared from recombinant virus-infected Sf9 cells as described by Ruppert et al., *Nature*, 362:175–179 (1993). Briefly, Sf9 cells are washed, resuspended in sonication buffer (25 mL Hepes, pH 7.9; 12.5 mM $MgCl_2$; 0.1 mM EDTA; 10% Glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 µm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or western blot with $Ni^{2+}$-NTA-conjugated to alkaline phosphatase (Qiagen). Fractions containing the eluted $His_{10}$-tagged IFN-ε are pooled and dialyzed against loading buffer.

Alternatively, purification of the IgG tagged (or Fc tagged) IFN-ε can be performed using known chromatography techniques, including for instance, Protein A or protein G column chromatography.

A specific protocol for purification of IgG-tagged proteins is as follows: The conditioned medium is filtered through a 0.45 micron filter, and loaded onto a Sepharose A column (Pharmacia). The column is washed with 5–6 CV 20 mM $NaH_2PO_4$, pH 6.8, and eluted with 3 CV 100 mM citric acid pH 3.4 After neutralization with 1 M Tris (pH 9.)) in fraction tubes (275 microliters per 1 ml fraction), the IFN-ε protein is desalted on PD-10 column.

Example 7

Preparation of Antibodies that Bind IFN-ε

This example illustrates preparation of monoclonal antibodies which can specifically bind IFN-ε.

Techniques for producing the monoclonal antibodies are known in the art and are described, for instance, in Goding, supra. Immunogens that may be employed include purified IFN-ε, fusion proteins containing IFN-ε, and cells expressing recombinant IFN-ε on the cell surface. Selection of the immunogen can be made by the skilled artisan without undue experimentation.

Mice, such as Balb/c, are immunized with the IFN-ε immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, MT) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-IFN-ε antibodies.

After a suitable antibody titer has been detected, the animals "positive" for antibodies can be injected with a final intravenous injection of IFN-ε. Three to four days later, the mice are sacrificed and the spleen cells are harvested. The spleen cells are then fused (using 35% polyethyleneglycol) to a selected murine myeloma cell line such as P3X63AgU. 1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against IFN-ε. Determination of "positive" hybridoma cells secreting the desired monoclonal antibodies against IFN-ε is within the skill in the art.

The positive hybridoma cells can be injected intraperitoneally into syngeneic Balb/c mice to produce ascites containing the anti-IFN-ε monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 8

Chromosomal Localization of IFN-ε

DNA from BAC clone F480 containing the IFN-ε gene, was labeled with digoxigenin dUTP followed by standard fluorescent in situ (FISH) hybridization procedure. (Knoll and Lichter, *Current Protocols in Human Genetics*, Dracopoli et al., eds., John Wiley & Sons, New York, 1995, Units 4.3.1–4.3.28; *Current Protocols in Molecular Biology*, Ausubel et al., eds., John Wiley & Sons, New York, 1997, Units 3.18; 14.7.1–14.7.14.) The initial experiment resulted in specific labeling of the short arm of a group C chromosome which was believed to be chromosome 9, based on size, morphology, and banding pattern. A second experiment was conducted in which a biotin-labeled probe which is specific for the heterochromatic region of chromosome 9 was co-hybridized with clone F480.

Figure 7B:
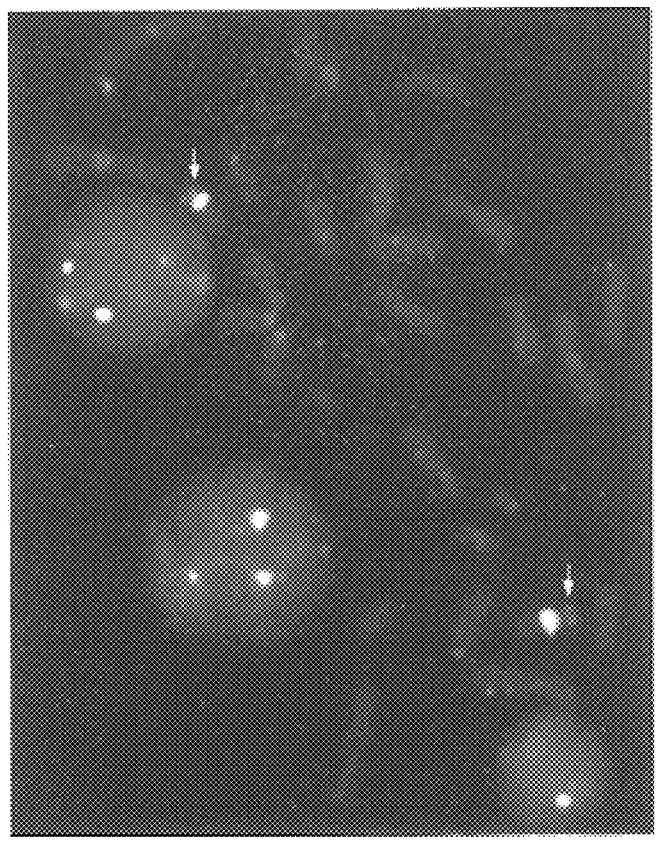

Measurements of 10 specifically labeled chromosomes 9 demonstrated that F480 is located at a position which is 51% of the distance from the centromere to the telomere of the 9p, an area which corresponds to chromosome 9p21.2–21.3 (FIG. 7(B)). A total of 80 metaphase cells were analyzed with 72 exhibiting specific labeling. The identified location is near other type 1 interferons (DeMaeyer, E. and De. Maeyer-Guignard, J., *Interferons. The Cytokine Handbook*, 2nd ed., 265–288 [1994]). Sequencing of the F480 BAC clone indicates that, like other type I interferons, the IFN-ε gene has no intervening sequences in its coding region.

Example 9

Northern Blot Analysis

The expression of IFN-ε in multiple tissues was examined by quantitative RT-PCR (Taqman Technology).

A multi-tissue RNA blot containing 2 μg each of poly(A)+ RNA from human tissues was purchased from Clontech. An overlapping oligo corresponding to codons for amino acid 2–31 in the IFN-ε precursor was generated. The DNA probes were labeled with $\alpha$-$^{32}$P=dCTP by random priming (Promega). The RNA blot was hybridized with 50% formamide, 5×SS, 50 mM potassium phosphate (pH 7.0), 5×Denhardt's solution, 10% dextran sulfate at 42° C. for 20 hours. The blot was washed with 0.1×SSC, 0.1% SDS at 50° C. for 30 minutes and exposed in Phospholmager.

The following tissues were examined: adult 1) heart, 2) brain, 3) placenta, 4) lung, 5) liver, 6) skeletal muscle, 7) kidney, 8) pancreas, 9) spleen, 10) thymus, 1 1) prostate, 12) testis, 13) ovary, 14) small intestine, 15) colon (mucosal lining), and 16) peripheral blood leukocytes, and human fetal tissues: 17) brain, 18) lung, 19) liver, and 20) kidney. Low levels of constitutive expression were detected in tissues of brain, lung, kidney, and small intestine (data not shown).

Example 10

Biological Activities of IFN-ε

Protocols

Expression and Purification of Recombinant IFN-ε in *E. coli*

IFN-ε was expressed in the *E. coli* cytoplasm, using a derivative of the tryptophan (trp) promoter vector pHGH207-1 (DeBoer et al., *Promoter Structure and Function*, Rodriguez et al., eds., p. 462, Praeger, New York, 1982.) A 210 amino acid leader sequence was fused to the amino termini of the mature interferon to ensure efficient translation initiation and to facilitate purification. This leader encodes the first 6 amino acids of the STII signal sequence (Picken et al., *H. Infect. Immun.* 42, 269–275 [1983]), followed by 8 histidines, and finally the amino acid sequence ASDDDDK for potential cleavage by the protease enterokinase. Downstream of the leader and mature IFN-ε coding sequences was placed the λto transcriptional terminator (Scholtissek and Grosse, *Nucl. Acids Res.* 15, 3185 [1987]).

The expression plasmid was transformed into the *E. coli* host 52A7 (W3110 fhuA(tonA) Ion galE rpoHts(htpRts) cIpP lacIq) prior to the induction of the trp promoter. Cells were first grown in LB containing ampicillin at 30° C. until a cell density of 2–4 ($A_{600}$) was reached. The LB culture was then diluted 20 fold into a high cell density tryptophan limiting media (per liter: 1.86 g $Na_2HPO_4$, 0.93 g $NaH_2PO_4H_2O$, 3.57 g $(NH_4)_2SO_4$, 0.71 g $Na_2Citrate(H_2O)_2$, 1.07 g KCl, 5.36 g yeast extract, 5.36 g casamino acids, autoclave, then add MOPS pH 7.3 to 110 mM, $NgSO_4$ to 7 mM, and glucose to 0.55% w/v). After 5 hours, trans-3-indoleacrylic acid was added to 50 μg/mL and then growth was continued for another 16 hours at 30° C. with shaking. The cells were then centrifuged and frozen until proceeding to Ni-column purification and refolding.

Expression and Purification of IFN-α Receptor (IFNAR) Immunoadhesins

Mammalian expression vectors encoding IFN-αR1-IgG1 and IFN-αR2-IgG (pRKIFN-α/β-IgG and pRKIFN-α/β-IgG) were constructed from plasmids encoding the human type 1 interferon receptors (pRKIFN-α/βR1 and pRKIFN-α/βR2) and CD4-IgG1 (pRKCD4$_2$Fc$_1$—Capon et al., *Nature* 337:525–531 [1989]). The mature IFN-α/βR1-IgG and IFN-α/βR2-IgG polypeptide encoded by pRK IFN-α/βR1-IgG and pRKIFN-α/βR2-IgG thus contain 633 and 443 amino acids, respectively. The IFN-α/βR-IgGs were expressed in human embryonic kidney 293 cells by transient transfection with the respective plasmids, using the calcium phosphate precipitation method. The receptor-IgG immunoadhesins were purified to greater than 95% homogeneity from serum-free cell supernatants by affinity chromatography on Staphylococcus aureus Protein A. The immunoadhesins were eluted with 50 mM sodium citrate pH 3/20% (w/v) glycerol, and the pH was neutralized with 0.05 volumes of 3M TRIS HCl (pH 8–9).

Tyrosine Phosphorylation Assay

Cells were serum-starved for 6 hours and subjected to treatment of cytokines for the indicated period of time, using the indicated concentrations. The lysis of cells, immunoprecipitation, Western blot and ECL detection were performed as previously described by Zhang et al., *Proc. Natl. Acad. Sci. USA* 94, 9562–7 (1997). The following antibodies were used: JAK1 (Q-19), JAK2 (HR758) Tyk2 (C-20), Stat1 (C-111), Stat2 (C-20) and Stat3 (C-20) purchased from Santa Cruz Biotechnology (CA). Antibody 4G10 was purchased from Upstate Biotechnology. anti-IFN-αR1 antibody 2E1.5.2 and anti-IFN-αR2 antibody 3B7.22.7were prepared as described in Lu J. et al., *J. Immunol.* 160: 1782–1788 (1988).

Electrophoretic Mobility Shift Assay (EMSA)

HelaS 3 (ATCC CCL2.2) cells were pretreated with IFN-γ(100 U/ml) overnight to increase the expression of p48 (Levy et al., *Genes Dev.* 3, 1362–71[1989]). Cells were treated with IFN-ε$^{His}$ or IFN-α for 45 minutes and nuclear extract was prepared. The preparation of nuclear extract and EMSA followed the protocol described by Levy, supra, with modifications (Zhang et al., *J. Biol. Chem.* 271, 9503–9509 [1996]). The probe for ESRE (ISG-15) and SIE is based on Darnell et al., *Science* 264, 1415–21 (1994).

Cell Culture, FACS Analysis and Cell Growth Inhibition Assay

Daudi cells, A549 cell and human 293 cell were growth in "5):5)" medium (HAM's F12: Dulbecco's Modified Eagle medium), with 10% FBS. Daudi cells, MELT-4 and U266 were growth in RPMI 1640, supplemented with 10–15% FBS. FACS analysis was performed as previously described (Zhang, 1997, supra). The anti-MHC I antibody (HLA-A, B, C) was purchased from Pharmacia. The growth inhibition assay was performed as described by Evinger and Pestka, *Methods Enzymol.* 79, 362–8 (1981). Briefly, Daudi cells were treated with different doses of IFNs and incubated at 37° C. for 72 hours. Cells were counted by Coulter cell counter to estimate growth.

Results

IFN-ε cDNA was expressed in bacteria as a His-tagged protein and subjected to purification. To determine whether IFN-ε can interact with known Type I IFN receptors, we treated U266 cells with the recombinant IFN-ε (designated IFN-ε$^{His}$) of various concentrations and immunoprecipitated IFN-α-R1 (IFNAR1) and IFN-α-R2 (IFNR2). The immunocomplexes were subjected to SDS-PAGE and detection of tyrosine phosphorylation (FIG. 8, Panels A and B). There was a dose-dependent tyrosine phosphorylation of both receptor subunits upon treatment with IFN-ε$^{His}$. This induction of receptor tyrosine phosphorylation was also time dependent, starting at less than 1 min after treatment and decreasing to undetectable level by 1 hr (data not shown). Similar results were obtained with other cell lines such as MALT-4 and Daudi cells (not shown).

Type I IFNs have been shown to activate JAK-STAT signaling components after interacting with their receptors. To examine whether IFN-ε activates the same signaling molecules, we assayed tyrosine phosphorylation of the key components in the IFN-α/β signal pathway. As shown in FIG. 8, Panels C and D, IFN-ε stimulated tyrosine phosphorylation of Janus kinase members JAK1 and Tyk2, but not JAK2 (not shown). It also caused the tyrosine phosphorylation of STAT family members Stat1, Stat2 and Stat3 (FIG. 8, Panels E, F and G). In addition, we examined the formation of transcription factor complexes ISGF3 and SIF upon treatment of HeLa cells with IFN-ε. (FIG. 8, Panels H–I.) Like IFN-α, IFN-ε stimulated the formation of both complexes that are able to bind corresponding DNA ciselements. These complexes can be specifically competed by excess amount of cold oligos and can be abolished or supershifted by anti-Stat antibodies. Therefore, IFN-ε is similar to IFN-α/β, in terms of activation of JAK-STAT pathway.

One way to demonstrate that the IFNAR1 and IFNAR2 are directly involved in the IFN-ε activation of JAK-STAT signaling is to block the functions of these receptors on the cell surface. For this purpose, we employed monoclonal antibodies against IFNAR2s that were developed to inhibit the biological responses (e.g., antivial response) of IFN-α. These antibodies recognized the corresponding receptor specifically (data now shown and FIG. 8, Panel J). Preincubation of MALT4 cells with either anti-IFNAR1 or anti-IFNAR2 antibodies (at 10 μg/ml) completely abolished IFN-ε-induced tyrosine phosphorylation of Stat2. In contrast, anti-IFNAR1 antibodies only partially inhibited IFN-α2a-induced Stat2 tyrosine phosphorylation although the inhibiting effect of anti-IFNAR2 antibodies is complete for IFN-α2a (FIG. 8, Panel J). This difference of IFNAR1 inhibition is more dramatic when lower concentrations of the inhibitory antibodies were used (not shown). We conclude from this experiment that IFNAR1 and IFNAR2 are necessary for IFN-ε to stimulate JAK-STAT pathway, although our results did not rule our the possibility that other receptor component(s) is/are involved in the IFN-ε-receptor interaction. Secondly, our observations suggest that there may be differences in terms of ligand-receptor engagement on the presence of certain amount of IFNAR1, IFN-α is more tolerable to blocking or inactivation of this receptor subunit.

Figure 9A:
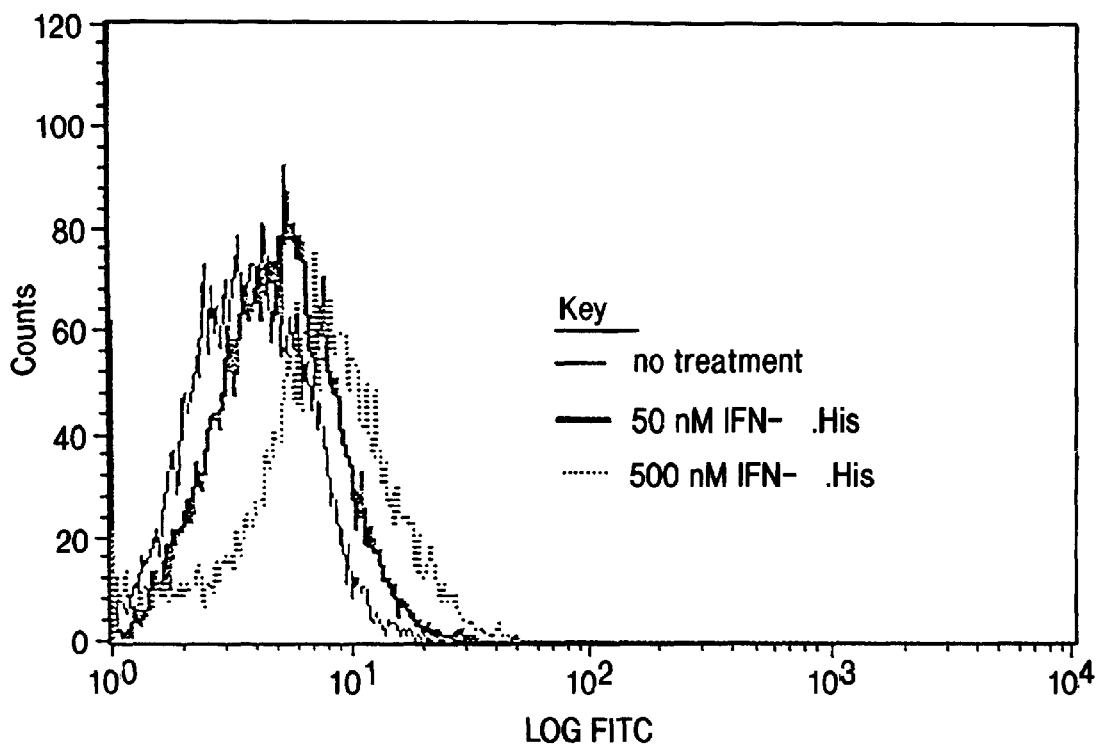
FIG. 9 shows that IFN-ε induces MHC I expression and exhibits growth inhibitory effect in cultured cells. (A) IFN-ε stimulates MHC I expression in MALT-4 cells. MALT-4 cells ($4 \times 10^5$/ml) were treated with indicated concentrations of IFN-ε$^{His}$ for 72 hours. FACS analysis was performed using FITC-conjugated anti-MHC I (HLA-A, B, C, Pharminogen). Similar results were obtained using 100–1000 U/ml of IFN-α$_{2a}$ (not shown). (B) IFN-ε has growth inhibitory effect on Daudi cells. Daudi cells ($4 \times 10^5$/ml) were either untreated (lane 1) or treated with 0.5 nM, 5 nM, 50 nM and 500 nM of IFN-ε$^{His}$ (lanes 2, 3, 4 and 5, respectively), or with 1 U/ml, 10 U/Ml, $10^2$ U/ml, $10^3$ U/ml of IFN-α$_{2a}$ (lanes 6, 7, 8, 9, respectively),for 72 hours. Total cell numbers were counted by Coulter counter. Error bar is standard deviation (n=4).

To explore the biological activities of IFN-ε, we treated various cell lines with IFN-ε$^{His}$ for 72 hr. Cells were evaluated for MHCI expression as an indication of immune modulation. IFN-ε induced the expression of MHC I in MALT-4 cells (FIG. 9A), and other cell lines (not shown).

Figure 9B:
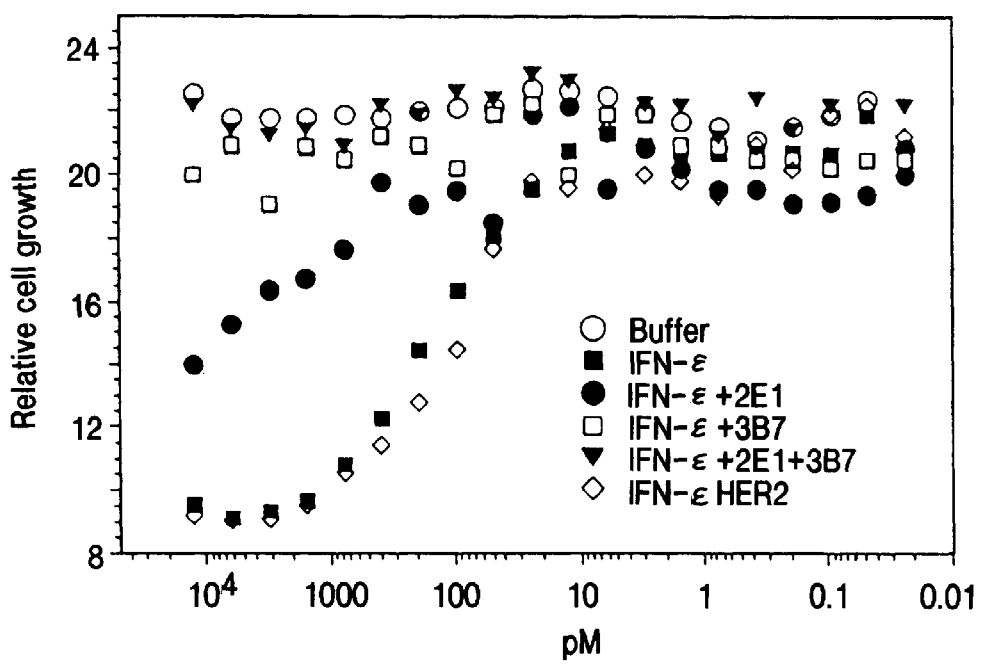

Since IFN-α/β have growth inhibitory effect for various cell types, we evaluated the growth inhibitory effect of IFN-ε. Daudi cells were treated with increasing concentrations of IFN-ε$^{His}$, relative cell growth was estimated by staining cells with Alamar Blue, a redox indicator which reflects relative cell numbers. As shown in FIG. 9B, IFN-ε inhibits the growth of Daudi cells in a dose-dependent manner with an IC50 of about 100 μM. Moreover, this growth inhibitory effect was partially abolished by 0.5 μg/ml of anti-IFNAR1 antibody 2E1, and completely abolished by anti-IFNAR2 antibody 3B7, but not by control antibody (HER2).

In summary, from analysis of sequence homology, chromosomal localization, receptor interaction, downstream signaling and biological effects, it can be concluded that IFN-ε belongs to a novel family of Type I IFNs. Although it shares common features with IFN-α/β, IFN-ε is unique in several aspects. The receptor interaction between IFN-ε and other Type I IFNs may differ, based on the low degree of sequence homology between the proteins and the differential inhibiting effect of anti-IFNAR antibodies towards IFN-ε and IFN-α. The difference in receptor binding could result in different biological responses in the same cell types. IFN-ε displays stronger activity in JAK-STAT activation, cell growth inhibition than antiviral action (data not shown), which supports the notion that different Type I IFNs play different, although possibly similar or overlapping, roles in vivo.

In this study, the EC50 that was needed for IFN-ε$^{His}$ to stimulate the same biological effect as purified IFN-α2 was higher. It is possible that in vivo, IFN-ε is expressed at higher levels in some tissues and thus the lower potency observed in vitro reflects the physiological situation. Alternatively, the nature of ligand-receptor interaction is different between IFN-ε and other Type I IFNs. In addition, IFN-ε$^{His}$ is a His-tagged recombinant protein, factors such as protein folding may affect specific activity. Further experiments are needed to elucidate the unique character of IFN-ε, which include detailed ligand-receptor interact ion studies and comparison of various activities between members of the Type I interferon family.

Deposit of Material

The following material has been deposited with the American Type Culture Collection, 12301 Parklawn Drive, Rockville, Md., USA (ATCC):

| Material | ATCC Dep. No. | Deposit Date |
| --- | --- | --- |
| DNA50960-1224 | 209509 | December 3, 1997 |

This deposit was made under the provisions of the Budapest Treaty on the International Recognition of the Deposit of Microorganisms for the Purpose of Patent Procedure and the Regulations thereunder(BudapestTreaty). This assures maintenance of a viable culture of the deposit for 30 years from the date of deposit. The deposit will be made available by ATCC under the terms of the BudapestTreaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

SEQUENCE LISTING

<160> NUMBER OF SEQ ID NOS: 24

<210> SEQ ID NO 1
<211> LENGTH: 208
<212> TYPE: PRT
<213> ORGANISM: Homo sapiens

<400> SEQUENCE: 1

```
Met Ile Ile Lys His Phe Phe Gly Thr Val Leu Val Leu Leu Ala Ser
 1               5                  10                  15

Thr Thr Ile Phe Ser Leu Asp Leu Lys Leu Ile Ile Phe Gln Gln Arg
            20                  25                  30

Gln Val Asn Gln Glu Ser Leu Lys Leu Leu Asn Lys Leu Gln Thr Leu
        35                  40                  45

Ser Ile Gln Gln Cys Leu Pro His Arg Lys Asn Phe Leu Leu Pro Gln
    50                  55                  60

Lys Ser Leu Ser Pro Gln Gln Tyr Gln Lys Gly His Thr Leu Ala Ile
65                  70                  75                  80

Leu His Glu Met Leu Gln Gln Ile Phe Ser Leu Phe Arg Ala Asn Ile
                85                  90                  95

Ser Leu Asp Gly Trp Glu Glu Asn His Thr Glu Lys Phe Leu Ile Gln
            100                 105                 110

Leu His Gln Gln Leu Glu Tyr Leu Glu Ala Leu Met Gly Leu Glu Ala
        115                 120                 125

Glu Lys Leu Ser Gly Thr Leu Gly Ser Asp Asn Leu Arg Leu Gln Val
    130                 135                 140

Lys Met Tyr Phe Arg Arg Ile His Asp Tyr Leu Glu Asn Gln Asp Tyr
145                 150                 155                 160

Ser Thr Cys Ala Trp Ala Ile Val Gln Val Glu Ile Ser Arg Cys Leu
                165                 170                 175

Phe Phe Val Phe Ser Leu Thr Glu Lys Leu Ser Lys Gln Gly Arg Pro
            180                 185                 190

Leu Asn Asp Met Lys Gln Glu Leu Thr Thr Glu Phe Arg Ser Pro Arg
        195                 200                 205
```

<210> SEQ ID NO 2
<211> LENGTH: 1502
<212> TYPE: DNA
<213> ORGANISM: Homo sapiens

<400> SEQUENCE: 2

```
cttagatatt aaactgatag gataagatat aaaataattt aagattgctg atatatgttt      60
taaaattaat tatttgctca agcatttgtg acaatttaca gttctaattg aggttttaaa     120
tttagtagtt tgtaggtatt ttaagttttg cccctgaatt ctttataggt gctgataagc     180
ctttggttaa gttttactcc atgaaagact attactgaaa aaaatgtaat ctcaataaaa     240
gaactttaat aagcttgact aaatatttag aaagcacatt gtgttcagtg aactttgta      300 tataatgaat agaataataa aagattatgt tggatgacta gtctgtaatt gcctcaagga     360
aagcatacaa tgaataagtt attttggtac ttcctcaaaa tagccaacac aatagggaaa     420
tggagaaaat gtactctgaa caccatgaaa agggaacctg aaaatctaat gtgtaaactt     480
ggagaaatga cattagaaaa cgaaagcaac aaaagagaac actctccaaa ataatctgag     540
atgcatgaaa ggcaaacatt cactagagct ggaatttccc taagtctatg cagggataag     600
```

```
tagcatattt gaccttcacc atgattatca agcacttctt tggaactgtg ttggtgctgc    660
tggcctctac cactatcttc tctctagatt tgaaactgat tatcttccag caaagacaag    720
tgaatcaaga aagtttaaaa ctcttgaata agttgcaaac cttgtcaatt cagcagtgtc    780
taccacacag gaaaaacttt ctgcttcctc agaagtcttt gagtcctcag cagtaccaaa    840
aaggacacac tctggccatt ctccatgaga tgcttcagca gatcttcagc ctcttcaggg    900
caaatatttc tctggatggt tgggaggaaa accacacgga gaattcctc attcaacttc     960 atcaacagct agaataccta gaagcactca tgggactgga agcagagaag ctaagtggta    1020
cttggggtag tgataaacctt agattacaag ttaaaatgta cttccgaagg atccatgatt   1080
acctggaaaa ccaggactac agcacctgtg cctgggccat tgtccaagta gaaatcagcc    1140
gatgtctgtt ctttgtgttc agtctcacag aaaaactgag caaacaagga agacccttga    1200
acgacatgaa gcaagagctt actacagagt ttagaagccc gaggtaggtg gagggactag    1260
aggacttctc cagacatgat tcttcataga gtggtaatac aatttatagt acaatcacat    1320
tgctttgatt ttgtgtatat atatatttat ctgagtttta agattgtgca tattgaccac    1380
aattgttttt attttgtaat gtggctttat atattctatc cattttaaat tgtttgtatg    1440
tcaaaataaa ttcattaata tggttgattc ttcaaaaaaa aaaaaaaaaa aaaaaaaaa     1500 aa                                                                   1502

<210> SEQ ID NO 3
<211> LENGTH: 1502
<212> TYPE: DNA
<213> ORGANISM: Homo sapiens

<400> SEQUENCE: 3
tttttttttt tttttttttt ttttttttg aagaatcaac catattaatg aatttatttt      60
gacatacaaa caatttaaaa tggatagaat atataaagcc acattacaaa ataaaaacaa    120
ttgtggtcaa tatgcacaat cttaaaactc agataaatat atatatacac aaaatcaaag    180
caatgtgatt gtactataaa ttgtattacc actctatgaa gaatcatgtc tggagaagtc    240
ctctagtccc tccacctacc tcgggcttct aaactctgta gtaagctctt gcttcatgtc    300
gttcaagggt cttccttgtt tgctcagttt ttctgtgaga ctgaacacaa agaacagaca    360
tcggctgatt tctacttgga caatggccca ggcacaggtg ctgtagtcct ggttttccag    420
gtaatcatgg atccttcgga agtacatttt aacttgtaat ctaaggttat cactacccaa    480
agtaccactt agcttctctg cttccagtcc catgagtgct tctaggtatt ctagctgttg    540
atgaagttga atgaggaatt tctccgtgtg gttttcctcc caaccatcca gagaaatatt    600
tgccctgaag aggctgaaga tctgctgaag catctcatgg agaatggcca gagtgtgtcc    660
tttttggtac tgctgaggac tcaaagactt ctgaggaagc agaaagtttt tcctgtgtgg    720
tagacactgc tgaattgaca aggtttgcaa cttattcaag agttttaaac tttcttgatt    780
cacttgtctt tgctggaaga taatcagttt caaatctaga gagaagatag tggtagaggc    840
cagcagcacc aacacagttc caaagaagtg cttgataatc atggtgaagg tcaaatatgc    900
tacttatccc tgcatagact tagggaaatt ccagctctag tgaatgtttg cctttcatgc    960
atctcagatt attttggaga gtgttctctt tgttgctttc gttttctaa tgtcatttct    1020 ccaagtttac acattagatt tcaggttcc cttttcatgg tgttcagagt acattttctc    1080
catttcccta ttgtgttggc tattttgagg aagtaccaaa ataacttatt cattgtatgc    1140
tttccttgag gcaattacag actagtcatc caacataatc ttttattatt ctattcatta    1200
```

-continued

```
tatacaaagt tcactgaac acaatgtgct ttctaaatat ttagtcaagc ttattaaagt   1260
tcttttattg agattacatt ttttcagta atagtctttc atggagtaaa acttaaccaa   1320
aggcttatca gcacctataa agaattcagg ggcaaaactt aaaataccta caaactacta   1380
aatttaaaac ctcaattaga actgtaaatt gtcacaaatg cttgagcaaa taattaattt   1440
taaaacatat atcagcaatc ttaaattatt ttatatctta tcctatcagt ttaatatcta   1500
ag                                                                 1502
```

<210> SEQ ID NO 4
<211> LENGTH: 25
<212> TYPE: DNA
<213> ORGANISM: Homo sapiens

<400> SEQUENCE: 4

```
tctctgcttc cagtcccatg agtgc                                          25
```

<210> SEQ ID NO 5
<211> LENGTH: 27
<212> TYPE: DNA
<213> ORGANISM: Homo sapiens

<400> SEQUENCE: 5

```
gcttccagtc ccatgagtgc ttctagg                                        27
```

<210> SEQ ID NO 6
<211> LENGTH: 50
<212> TYPE: DNA
<213> ORGANISM: Homo sapiens

<400> SEQUENCE: 6

```
ggccattctc catgagatgc ttcagcagat cttcagcctc ttcagggcaa               50
```

<210> SEQ ID NO 7
<211> LENGTH: 187
<212> TYPE: PRT
<213> ORGANISM: Homo sapiens

<400> SEQUENCE: 7

```
Met Thr Asn Lys Cys Leu Leu Gln Ile Ala Leu Leu Cys Phe Ser
 1               5                  10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
```

```
                145                 150                 155                 160
His Cys Ala Trp Thr Ile Val Arg Val Glu Ile Leu Arg Asn Phe Tyr
                165                 170                 175
Phe Ile Asn Arg Leu Thr Gly Tyr Leu Arg Asn
                180                 185

<210> SEQ ID NO 8
<211> LENGTH: 189
<212> TYPE: PRT
<213> ORGANISM: Homo sapiens

<400> SEQUENCE: 8

Met Ala Ser Pro Phe Ala Leu Leu Met Val Leu Val Val Leu Ser Cys
  1               5                  10                  15

Lys Ser Ser Cys Ser Leu Gly Cys Asp Leu Pro Glu Thr His Ser Leu
                 20                  25                  30

Asp Asn Arg Arg Thr Leu Met Leu Leu Ala Gln Met Ser Arg Ile Ser
             35                  40                  45

Pro Ser Ser Cys Leu Met Asp Arg His Asp Phe Gly Phe Pro Gln Glu
         50                  55                  60

Glu Phe Asp Gly Asn Gln Phe Gln Lys Ala Pro Ala Ile Ser Val Leu
 65                  70                  75                  80

His Glu Leu Ile Gln Gln Ile Phe Asn Leu Phe Thr Thr Lys Asp Ser
                 85                  90                  95

Ser Ala Ala Trp Asp Glu Asp Leu Leu Asp Lys Phe Cys Thr Glu Leu
                100                 105                 110

Tyr Gln Gln Leu Asn Asp Leu Glu Ala Cys Val Met Gln Glu Glu Arg
            115                 120                 125

Val Gly Glu Thr Pro Leu Met Asn Ala Asp Ser Ile Leu Ala Val Lys
        130                 135                 140

Lys Tyr Phe Arg Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Leu Ser Thr Asn Leu Gln Glu Arg Leu Arg Arg Lys Glu
                180                 185

<210> SEQ ID NO 9
<211> LENGTH: 188
<212> TYPE: PRT
<213> ORGANISM: Homo sapiens

<400> SEQUENCE: 9

Met Ala Leu Thr Phe Ala Leu Leu Val Ala Leu Leu Val Leu Ser Cys
  1               5                  10                  15

Lys Ser Ser Cys Ser Val Gly Cys Asp Leu Pro Gln Thr His Ser Leu
                 20                  25                  30

Gly Ser Arg Arg Thr Leu Met Leu Leu Ala Gln Met Arg Lys Ile Ser
             35                  40                  45

Leu Phe Ser Cys Leu Lys Asp Arg His Asp Phe Gly Phe Pro Gln Glu
         50                  55                  60

Glu Phe Gly Asn Gln Phe Gln Lys Ala Glu Thr Ile Pro Val Leu His
 65                  70                  75                  80

Glu Met Ile Gln Gln Ile Phe Asn Leu Phe Ser Thr Lys Asp Ser Ser
                 85                  90                  95

Ala Ala Trp Asp Glu Thr Leu Leu Asp Lys Phe Tyr Thr Glu Leu Tyr
```

-continued

```
                  100                 105                 110
Gln Gln Leu Asn Asp Leu Glu Ala Cys Val Ile Gln Gly Val Gly Val
            115                 120                 125
Thr Glu Thr Pro Leu Met Lys Glu Asp Ser Ile Leu Ala Val Arg Lys
        130                 135                 140
Tyr Phe Gln Arg Ile Thr Leu Tyr Leu Lys Glu Lys Tyr Ser Pro
145                 150                 155                 160
Cys Ala Trp Glu Val Val Arg Ala Glu Ile Met Arg Ser Phe Ser Leu
                165                 170                 175
Ser Thr Asn Leu Gln Ser Leu Arg Ser Lys Glu
            180                 185

<210> SEQ ID NO 10
<211> LENGTH: 189
<212> TYPE: PRT
<213> ORGANISM: Homo sapiens

<400> SEQUENCE: 10

Met Ala Leu Ser Phe Ser Leu Leu Met Ala Val Leu Val Leu Ser Tyr
  1               5                  10                  15
Lys Ser Ile Cys Ser Leu Gly Cys Asp Leu Pro Gln Thr His Ser Leu
                20                  25                  30
Gly Asn Arg Arg Ala Leu Ile Leu Leu Ala Gln Met Gly Arg Ile Ser
            35                  40                  45
His Phe Ser Cys Leu Lys Asp Arg His Asp Phe Gly Phe Pro Glu Glu
        50                  55                  60
Glu Phe Asp Gly His Gln Phe Gln Lys Thr Gln Ala Ile Ser Val Leu
65                  70                  75                  80
His Glu Met Ile Gln Gln Thr Phe Asn Leu Phe Ser Thr Glu Asp Ser
                85                  90                  95
Ser Ala Ala Trp Glu Gln Ser Leu Leu Glu Lys Phe Ser Thr Glu Leu
                100                 105                 110
Tyr Gln Gln Leu Asn Asp Leu Glu Ala Cys Val Ile Gln Glu Val Gly
            115                 120                 125
Val Glu Glu Thr Pro Leu Met Asn Val Asp Ser Ile Leu Ala Val Arg
        130                 135                 140
Lys Tyr Phe Gln Arg Ile Thr Leu Tyr Leu Thr Glu Lys Lys Tyr Ser
145                 150                 155                 160
Pro Cys Ala Trp Glu Val Val Arg Ala Glu Ile Met Arg Ser Leu Ser
                165                 170                 175
Phe Ser Thr Asn Leu Gln Lys Arg Leu Arg Arg Lys Asp
            180                 185

<210> SEQ ID NO 11
<211> LENGTH: 189
<212> TYPE: PRT
<213> ORGANISM: Homo sapiens

<400> SEQUENCE: 11

Met Ala Leu Pro Phe Val Leu Leu Met Ala Leu Val Val Leu Asn Cys
  1               5                  10                  15
Lys Ser Ile Cys Ser Leu Gly Cys Asp Leu Pro Gln Thr His Ser Leu
                20                  25                  30
Ser Asn Arg Arg Thr Leu Met Ile Met Ala Gln Met Gly Arg Ile Ser
            35                  40                  45
Pro Phe Ser Cys Leu Lys Asp Arg His Asp Phe Gly Phe Pro Gln Glu
```

-continued

```
                50                  55                  60
Glu Phe Asp Gly Asn Gln Phe Gln Lys Ala Gln Ala Ile Ser Val Leu
 65                  70                  75                  80

His Glu Met Ile Gln Gln Thr Phe Asn Leu Phe Ser Thr Lys Asp Ser
                 85                  90                  95

Ser Ala Thr Trp Asp Glu Thr Leu Leu Asp Lys Phe Tyr Thr Glu Leu
                100                 105                 110

Tyr Gln Gln Leu Asn Asp Leu Glu Ala Cys Met Met Gln Glu Val Gly
                115                 120                 125

Val Glu Asp Thr Pro Leu Met Asn Val Asp Ser Ile Leu Thr Val Arg
                130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Phe Ser
                165                 170                 175

Leu Ser Ala Asn Leu Gln Glu Arg Leu Arg Arg Lys Glu
                180                 185
```

<210> SEQ ID NO 12
<211> LENGTH: 189
<212> TYPE: PRT
<213> ORGANISM: Homo sapiens

<400> SEQUENCE: 12

```
Met Ala Leu Pro Phe Ala Leu Leu Met Ala Leu Val Val Leu Ser Cys
 1                   5                  10                  15

Lys Ser Ser Cys Ser Leu Asp Cys Asp Leu Pro Gln Thr His Ser Leu
                 20                  25                  30

Gly His Arg Arg Thr Met Met Leu Leu Ala Gln Met Arg Arg Ile Ser
                 35                  40                  45

Leu Phe Ser Cys Leu Lys Asp Arg His Asp Phe Arg Phe Pro Gln Glu
                 50                  55                  60

Glu Phe Asp Gly Asn Gln Phe Gln Lys Ala Glu Ala Ile Ser Val Leu
 65                  70                  75                  80

His Glu Val Ile Gln Gln Thr Phe Asn Leu Phe Ser Thr Lys Asp Ser
                 85                  90                  95

Ser Val Ala Trp Asp Glu Arg Leu Leu Asp Lys Leu Tyr Thr Glu Leu
                100                 105                 110

Tyr Gln Gln Leu Asn Asp Leu Glu Ala Cys Val Met Gln Glu Val Trp
                115                 120                 125

Val Gly Gly Thr Pro Leu Met Asn Glu Asp Ser Ile Leu Ala Val Arg
                130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Phe Ser
                165                 170                 175

Ser Ser Arg Asn Leu Gln Glu Arg Leu Arg Arg Lys Glu
                180                 185
```

<210> SEQ ID NO 13
<211> LENGTH: 189
<212> TYPE: PRT
<213> ORGANISM: Homo sapiens

<400> SEQUENCE: 13

Met Ala Arg Ser Phe Ser Leu Leu Met Val Val Leu Val Leu Ser Tyr

```
                1               5                   10                  15
Lys Ser Ile Cys Ser Leu Gly Cys Asp Leu Pro Gln Thr His Ser Leu
                    20                  25                  30

Arg Asn Arg Arg Ala Leu Ile Leu Leu Ala Gln Met Gly Arg Ile Ser
                35                  40                  45

Pro Phe Ser Cys Leu Lys Asp Arg His Glu Phe Arg Phe Pro Glu Glu
            50                  55                  60

Glu Phe Asp Gly His Gln Phe Gln Lys Thr Gln Ala Ile Ser Val Leu
65                      70                  75                  80

His Glu Met Ile Gln Gln Thr Phe Asn Leu Phe Ser Thr Glu Asp Ser
                    85                  90                  95

Ser Ala Ala Trp Glu Gln Ser Leu Leu Glu Lys Phe Ser Thr Glu Leu
                100                 105                 110

Tyr Gln Gln Leu Asn Asp Leu Glu Ala Cys Val Ile Gln Glu Val Gly
                115                 120                 125

Val Glu Glu Thr Pro Leu Met Asn Glu Asp Phe Ile Leu Ala Val Arg
            130                 135                 140

Lys Tyr Phe Gln Arg Ile Thr Leu Tyr Leu Met Glu Lys Lys Tyr Ser
145                 150                 155                 160

Pro Cys Ala Trp Glu Val Val Arg Ala Glu Ile Met Arg Ser Phe Ser
                165                 170                 175

Phe Ser Thr Asn Leu Lys Lys Gly Leu Arg Arg Lys Asp
                180                 185

<210> SEQ ID NO 14
<211> LENGTH: 189
<212> TYPE: PRT
<213> ORGANISM: Homo sapiens

<400> SEQUENCE: 14

Met Ala Leu Thr Phe Tyr Leu Leu Val Ala Leu Val Val Leu Ser Tyr
1               5                   10                  15

Lys Ser Phe Ser Ser Leu Gly Cys Asp Leu Pro Gln Thr His Ser Leu
                    20                  25                  30

Gly Asn Arg Arg Ala Leu Ile Leu Leu Ala Gln Met Arg Arg Ile Ser
                35                  40                  45

Pro Phe Ser Cys Leu Lys Asp Arg His Asp Phe Glu Phe Pro Gln Glu
            50                  55                  60

Glu Phe Asp Asp Lys Gln Phe Gln Lys Ala Gln Ala Ile Ser Val Leu
65                      70                  75                  80

His Glu Met Ile Gln Gln Thr Phe Asn Leu Phe Ser Thr Lys Asp Ser
                    85                  90                  95

Ser Ala Ala Leu Asp Glu Thr Leu Leu Asp Glu Phe Tyr Ile Glu Leu
                100                 105                 110

Asp Gln Gln Leu Asn Asp Leu Glu Ser Cys Val Met Gln Glu Val Gly
                115                 120                 125

Val Ile Glu Ser Pro Leu Met Tyr Glu Asp Ser Ile Leu Ala Val Arg
            130                 135                 140

Lys Tyr Phe Gln Arg Ile Thr Leu Tyr Leu Thr Glu Lys Lys Tyr Ser
145                 150                 155                 160

Ser Cys Ala Trp Glu Val Val Arg Ala Glu Ile Met Arg Ser Phe Ser
                165                 170                 175

Leu Ser Ile Asn Leu Gln Lys Arg Leu Lys Ser Lys Glu
                180                 185
```

```
<210> SEQ ID NO 15
<211> LENGTH: 189
<212> TYPE: PRT
<213> ORGANISM: Homo sapiens

<400> SEQUENCE: 15

Met Ala Leu Ser Phe Ser Leu Leu Met Ala Val Leu Val Leu Ser Tyr
1               5                   10                  15

Lys Ser Ile Cys Ser Leu Gly Cys Asp Leu Pro Gln Thr His Ser Leu
            20                  25                  30

Gly Asn Arg Arg Ala Leu Ile Leu Leu Gly Gln Met Gly Arg Ile Ser
        35                  40                  45

Pro Phe Ser Cys Leu Lys Asp Arg His Asp Phe Arg Ile Pro Gln Glu
    50                  55                  60

Glu Phe Asp Gly Asn Gln Phe Gln Lys Ala Gln Ala Ile Ser Val Leu
65                  70                  75                  80

His Glu Met Ile Gln Gln Thr Phe Asn Leu Phe Ser Thr Glu Asp Ser
                85                  90                  95

Ser Ala Ala Trp Glu Gln Ser Leu Leu Glu Lys Phe Ser Thr Glu Leu
            100                 105                 110

Tyr Gln Gln Leu Asn Asp Leu Glu Ala Cys Val Ile Gln Glu Val Gly
        115                 120                 125

Val Glu Glu Thr Pro Leu Met Asn Glu Asp Ser Ile Leu Ala Val Arg
    130                 135                 140

Lys Tyr Phe Gln Arg Ile Thr Leu Tyr Leu Ile Glu Arg Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
            180                 185

<210> SEQ ID NO 16
<211> LENGTH: 189
<212> TYPE: PRT
<213> ORGANISM: Homo sapiens

<400> SEQUENCE: 16

Met Ala Leu Pro Phe Ala Leu Met Met Ala Leu Val Val Leu Ser Cys
1               5                   10                  15

Lys Ser Ser Cys Ser Leu Gly Cys Asn Leu Ser Gln Thr His Ser Leu
            20                  25                  30

Asn Asn Arg Arg Thr Leu Met Leu Met Ala Gln Met Arg Arg Ile Ser
        35                  40                  45

Pro Phe Ser Cys Leu Lys Asp Arg His Asp Phe Glu Phe Pro Gln Glu
    50                  55                  60

Glu Phe Asp Gly Asn Gln Phe Gln Lys Ala Gln Ala Ile Ser Val Leu
65                  70                  75                  80

His Glu Met Met Gln Gln Thr Phe Asn Leu Phe Ser Thr Lys Asn Ser
                85                  90                  95

Ser Ala Ala Trp Asp Glu Thr Leu Leu Glu Lys Phe Tyr Ile Glu Leu
            100                 105                 110

Phe Gln Gln Met Asn Asp Leu Glu Ala Cys Val Ile Gln Glu Val Gly
        115                 120                 125

Val Glu Glu Thr Pro Leu Met Asn Glu Asp Ser Ile Leu Ala Val Lys
    130                 135                 140
```

```
Lys Tyr Phe Gln Arg Ile Thr Leu Tyr Leu Met Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Arg Leu Arg Arg Lys Asp
                180                 185
```

<210> SEQ ID NO 17
<211> LENGTH: 189
<212> TYPE: PRT
<213> ORGANISM: Homo sapiens

<400> SEQUENCE: 17

```
Met Ala Leu Ser Phe Ser Leu Leu Met Ala Val Leu Val Leu Ser Tyr
 1               5                  10                  15

Lys Ser Ile Cys Ser Leu Gly Cys Asp Leu Pro Gln Thr His Ser Leu
                 20                  25                  30

Gly Asn Arg Arg Ala Leu Ile Leu Leu Ala Gln Met Gly Arg Ile Ser
             35                  40                  45

His Phe Ser Cys Leu Lys Asp Arg Tyr Asp Phe Gly Phe Pro Gln Glu
         50                  55                  60

Val Phe Asp Gly Asn Gln Phe Gln Lys Ala Gln Ala Ile Ser Ala Phe
 65                  70                  75                  80

His Glu Met Ile Gln Gln Thr Phe Asn Leu Phe Ser Thr Lys Asp Ser
                 85                  90                  95

Ser Ala Ala Trp Asp Glu Thr Leu Leu Asp Lys Phe Tyr Ile Glu Leu
                100                 105                 110

Phe Gln Gln Leu Asn Asp Leu Glu Ala Cys Val Thr Gln Glu Val Gly
            115                 120                 125

Val Glu Glu Ile Ala Leu Met Asn Glu Asp Ser Ile Leu Ala Val Arg
130                 135                 140

Lys Tyr Phe Gln Arg Ile Thr Leu Tyr Leu Met Gly Lys Lys Tyr Ser
145                 150                 155                 160

Pro Cys Ala Trp Glu Val Val Arg Ala Glu Ile Met Arg Ser Phe Ser
                165                 170                 175

Phe Ser Thr Asn Leu Gln Lys Gly Leu Arg Arg Lys Asp
                180                 185
```

<210> SEQ ID NO 18
<211> LENGTH: 189
<212> TYPE: PRT
<213> ORGANISM: Homo sapiens

<400> SEQUENCE: 18

```
Met Ala Leu Ser Phe Ser Leu Leu Met Ala Val Leu Val Leu Ser Tyr
 1               5                  10                  15

Lys Ser Ile Cys Ser Leu Gly Cys Asp Leu Pro Gln Thr His Ser Leu
                 20                  25                  30

Gly Asn Arg Arg Ala Leu Ile Leu Leu Ala Gln Met Gly Arg Ile Ser
             35                  40                  45

Pro Phe Ser Cys Leu Lys Asp Arg His Asp Phe Gly Leu Pro Gln Glu
         50                  55                  60

Glu Phe Asp Gly Asn Gln Phe Gln Lys Thr Gln Ala Ile Ser Val Leu
 65                  70                  75                  80

His Glu Met Ile Gln Gln Thr Phe Asn Leu Phe Ser Thr Glu Asp Ser
                 85                  90                  95
```

```
Ser Ala Ala Trp Glu Gln Ser Leu Leu Glu Lys Phe Ser Thr Glu Leu
            100                 105                 110

Tyr Gln Gln Leu Asn Asn Leu Glu Ala Cys Val Ile Gln Glu Val Gly
        115                 120                 125

Met Glu Glu Thr Pro Leu Met Asn Glu Asp Ser Ile Leu Ala Val Arg
130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Leu Ser
                165                 170                 175

Phe Ser Thr Asn Leu Gln Lys Ile Leu Arg Arg Lys Asp
                180                 185

<210> SEQ ID NO 19
<211> LENGTH: 189
<212> TYPE: PRT
<213> ORGANISM: Homo sapiens

<400> SEQUENCE: 19

Met Ala Leu Ser Phe Ser Leu Leu Met Ala Val Leu Val Leu Ser Tyr
1               5                   10                  15

Lys Ser Ile Cys Ser Leu Gly Cys Asp Leu Pro Gln Thr His Ser Leu
            20                  25                  30

Gly Asn Arg Arg Ala Leu Ile Leu Leu Ala Gln Met Gly Arg Ile Ser
        35                  40                  45

Pro Phe Ser Cys Leu Lys Asp Arg His Asp Phe Gly Phe Pro Gln Glu
    50                  55                  60

Glu Phe Asp Gly Asn Gln Phe Gln Lys Ala Gln Ala Ile Ser Val Leu
65                  70                  75                  80

His Glu Met Ile Gln Gln Thr Phe Asn Leu Phe Ser Thr Lys Asp Ser
                85                  90                  95

Ser Ala Thr Trp Glu Gln Ser Leu Leu Glu Lys Phe Ser Thr Glu Leu
            100                 105                 110

Asn Gln Gln Leu Asn Asp Met Glu Ala Cys Val Ile Gln Glu Val Gly
        115                 120                 125

Val Glu Glu Thr Pro Leu Met Asn Val Asp Ser Ile Leu Ala Val Lys
130                 135                 140

Lys Tyr Phe Gln Arg Ile Thr Leu Tyr Leu Thr Glu Lys Lys Tyr Ser
145                 150                 155                 160

Pro Cys Ala Trp Glu Val Val Arg Ala Glu Ile Met Arg Ser Phe Ser
                165                 170                 175

Leu Ser Lys Ile Phe Gln Glu Arg Leu Arg Arg Lys Glu
                180                 185

<210> SEQ ID NO 20
<211> LENGTH: 276
<212> TYPE: DNA
<213> ORGANISM: Homo sapiens

<400> SEQUENCE: 20
aaactttctg cttcctcaga agtctttgag tcctcagcag taccaaaaag gacacactct      60
ggccattctc catgagatgc ttcagcagat cttcagcctc ttcagggcaa atatttctct     120
ggatggttgg gaggaaaacc acacggagaa attcctcatt cancttcatc aacagctaga     180
atacctagaa gcactcatgg gactggaagc agagaagcta agtggtactt tgggtagtga     240
taaccttaga ttacaagtta aaatgtactt ccgaag                                276
```

<210> SEQ ID NO 21
<211> LENGTH: 276
<212> TYPE: DNA
<213> ORGANISM: Homo sapiens

<400> SEQUENCE: 21

```
cttcggaagt acattttaac ttgtaatcta aggttatcac tacccaaagt accacttagc      60
ttctctgctt ccagtcccat gagtgcttct aggtattcta gctgttgatg aagntgaatg     120
aggaatttct ccgtgtggtt ttcctcccaa ccatccagaa aaatatttgc cctgaagagg     180
ctgaagatct gctgaagcat ctcatggaga atggccagag tgtgtccttt ttggtactgc     240
tgaggactca aagacttctg aggaagcaga aagttt                              276
```

<210> SEQ ID NO 22
<211> LENGTH: 91
<212> TYPE: PRT
<213> ORGANISM: Homo sapiens

<400> SEQUENCE: 22

Asn Phe Leu Leu Pro Gln Lys Ser Leu Ser Pro Gln Gln Tyr Gln Lys
 1               5                  10                  15

Gly His Thr Leu Ala Ile Leu His Glu Met Leu Gln Gln Ile Phe Ser
            20                  25                  30

Leu Phe Arg Ala Asn Ile Ser Leu Asp Gly Trp Glu Glu Asn His Thr
        35                  40                  45

Glu Lys Phe Leu Ile Xaa Leu His Gln Gln Leu Glu Tyr Leu Glu Ala
    50                  55                  60

Leu Met Gly Leu Glu Ala Glu Lys Leu Ser Gly Thr Leu Gly Ser Asp
65                  70                  75                  80

Asn Leu Arg Leu Gln Val Lys Met Tyr Phe Arg
                85                  90

<210> SEQ ID NO 23
<211> LENGTH: 195
<212> TYPE: PRT
<213> ORGANISM: Homo sapiens

<400> SEQUENCE: 23

Met Ala Leu Leu Phe Pro Leu Leu Ala Ala Leu Val Met Thr Ser Tyr
 1               5                  10                  15

Ser Pro Val Gly Ser Leu Gly Cys Asp Leu Pro Gln Asn His Gly Leu
            20                  25                  30

Leu Ser Arg Asn Thr Leu Val Leu Leu His Gln Met Arg Arg Ile Ser
        35                  40                  45

Pro Phe Leu Cys Leu Lys Asp Arg Arg Asp Phe Arg Phe Pro Gln Glu
    50                  55                  60

Met Val Lys Gly Ser Gln Leu Gln Lys Ala His Val Met Ser Val Leu
65                  70                  75                  80

His Glu Met Leu Gln Gln Ile Phe Ser Leu Phe His Thr Glu Arg Ser
                85                  90                  95

Ser Ala Ala Trp Asn Met Thr Leu Leu Asp Gln Leu His Thr Gly Leu
            100                 105                 110

His Gln Gln Leu Gln His Leu Glu Thr Cys Leu Leu Gln Val Val Gly
        115                 120                 125

Glu Gly Glu Ser Ala Gly Ala Ile Ser Ser Pro Ala Leu Thr Leu Arg
    130                 135                 140

```
Arg Tyr Phe Gln Gly Ile Arg Val Tyr Leu Lys Glu Lys Lys Tyr Ser
145                 150                 155                 160

Asp Cys Ala Trp Glu Val Val Arg Met Glu Ile Met Lys Ser Leu Phe
                165                 170                 175

Leu Ser Thr Asn Met Gln Glu Arg Leu Arg Ser Lys Asp Arg Asp Leu
                180                 185                 190

Gly Ser Ser
        195

<210> SEQ ID NO 24
<211> LENGTH: 166
<212> TYPE: PRT
<213> ORGANISM: Homo sapiens

<400> SEQUENCE: 24

Met Lys Tyr Thr Ser Tyr Ile Leu Ala Phe Gln Leu Cys Ile Val Leu
  1               5                  10                  15

Gly Ser Leu Gly Cys Tyr Cys Gln Asp Pro Tyr Val Lys Glu Ala Glu
                 20                  25                  30

Asn Leu Lys Lys Tyr Phe Asn Ala Gly His Ser Asp Val Ala Asp Asn
             35                  40                  45

Gly Thr Leu Phe Leu Gly Ile Leu Lys Asn Trp Lys Glu Glu Ser Asp
         50                  55                  60

Arg Lys Ile Met Gln Ser Gln Ile Val Ser Phe Tyr Phe Lys Leu Phe
 65                  70                  75                  80

Lys Asn Phe Lys Asp Asp Gln Ser Ile Gln Lys Ser Val Glu Thr Ile
                 85                  90                  95

Lys Glu Asp Met Asn Val Lys Phe Phe Asn Ser Asn Lys Lys Lys Arg
                100                 105                 110

Asp Asp Phe Glu Lys Leu Thr Asn Tyr Ser Val Thr Asp Leu Asn Val
            115                 120                 125

Gln Arg Lys Ala Ile His Glu Leu Ile Gln Val Met Ala Glu Leu Ser
        130                 135                 140

Pro Ala Ala Lys Thr Gly Lys Arg Lys Arg Ser Gln Met Leu Phe Arg
145                 150                 155                 160

Gly Arg Arg Ala Ser Gln
                165
```

What is claimed is:

1. An antibody which specifically binds to an IFN-ε polypeptide, wherein said polypeptide comprises an amino acid sequence having at least 80% amino acid sequence identity with the sequence of amino acids from about 22 to 189 of SEQ ID NO:1 and further has the ability to activate components of the JAK-STAT pathway as determined by phosphorylation of JAK1, Tyk 2, STAT1, STAT2, or STAT3.

2. The antibody of claim 1 wherein said antibody is a monoclonal antibody.

3. The antibody of claim 1, wherein said polypeptide comprises the sequence of amino acids from about 22 to 189 of SEQ ID NO:1.

4. An antibody which binds to an IFN-ε polypeptide, wherein said polypeptide comprises an amino acid sequence encoded by a nucleic acid sequence which binds under high stringency conditions comprising hybridization in a solution of 50% formamide, 5×SSC, 0.1% SDS, 0.1% sodium pyrophosphate, 50 mM sodium phosphate, pH 6.0, 2×Denhardt's solution, and 10% dextran sulfate at 42° C. for 20 hours and washing in an aqueous solution of 0.1 SSC and 0.1% SDS at 42° C. to a nucleic acid sequence which encodes the sequence of amino acids from about 22 to 189 of SEQ ID NO:1, or the complement thereof.

5. The antibody of claim 4, wherein said polypeptide comprises the sequence of amino acids from about 22 to 189 of SEQ ID NO:1.

6. The antibody as in claim 1 or 4, wherein said antibody is a human antibody.

7. The antibody as in claim 1 or 4, wherein said antibody is a humanized antibody.

8. The antibody as in claim 1 or 4, wherein said antibody is an antagoinst of IFN-ε.

9. A composition comprising the antibody as in claim 1 or 4 and a physiologically acceptable vehicle.

10. The antibody as in claim 1 or 4 which is immobilized on an insoluble matrix.

11. The antibody as in claim 1 or 4 which is bound to a detectable label.

12. A method for determining the presence of IFN-ε polypeptide comprising exposing a cell suspected of containing the IFN-ε polypeptide to the antibody as in claim 1 or 4 and determining binding of said antibody to said cell.

13. A method for purifying IFN-ε polypeptide comprising passing a sample comprising said IFN-ε polypeptide over a support to which the antibody as in claim 1 or 4 is bound.

* * * * *